(12) United States Patent
Ratnakar

(10) Patent No.: US 11,606,497 B2
(45) Date of Patent: Mar. 14, 2023

(54) ENDOSCOPE WITH MULTIPLE VIEWS AND NOVEL CONFIGURATIONS ADAPTED THERETO

(71) Applicant: Nitesh Ratnakar, Wheeling, WV (US)

(72) Inventor: Nitesh Ratnakar, Wheeling, WV (US)

( * ) Notice: Subject to any disclaimer, the term of this patent is extended or adjusted under 35 U.S.C. 154(b) by 0 days.

(21) Appl. No.: 14/736,258

(22) Filed: Jun. 10, 2015

(65) Prior Publication Data

US 2016/0006943 A1    Jan. 7, 2016

Related U.S. Application Data

(60) Provisional application No. 62/158,513, filed on May 7, 2015, provisional application No. 62/117,953, filed on Feb. 18, 2015, provisional application No. 62/010,396, filed on Jun. 10, 2014.

(51) Int. Cl.
| | | |
|---|---|---|
| *A61B 1/05* | (2006.01) | |
| *H04N 5/232* | (2006.01) | |
| *H04N 5/247* | (2006.01) | |
| *A61B 1/045* | (2006.01) | |
| *G06T 3/40* | (2006.01) | |
| *A61B 1/00* | (2006.01) | |
| *A61B 1/12* | (2006.01) | |
| *A61B 1/06* | (2006.01) | |
| *H04N 5/265* | (2006.01) | |
| *A61B 1/018* | (2006.01) | |
| *G02B 23/24* | (2006.01) | |
| *H04N 5/225* | (2006.01) | |

(52) U.S. Cl.
CPC ...... *H04N 5/23238* (2013.01); *A61B 1/00009* (2013.01); *A61B 1/00181* (2013.01); *A61B 1/045* (2013.01); *A61B 1/0625* (2022.02); *A61B 1/0655* (2022.02); *A61B 1/126* (2013.01); *G06T 3/4038* (2013.01); *H04N 5/247* (2013.01); *A61B 1/00124* (2013.01); *A61B 1/018* (2013.01); *G02B 23/2423* (2013.01); *H04N 5/265* (2013.01); *H04N 2005/2255* (2013.01)

(58) Field of Classification Search
CPC ............... H04N 5/23238; H04N 5/247; A61B 1/00009; A61B 1/00181; A61B 1/045; A61B 1/126; G06T 3/4038
See application file for complete search history.

(56) References Cited

U.S. PATENT DOCUMENTS

2015/0062299 A1*   3/2015  Brown .............. A61B 1/00009
                                                             348/45

* cited by examiner

*Primary Examiner* — Christopher G Findley
(74) *Attorney, Agent, or Firm* — Jundong Ma

(57) ABSTRACT

Disclosed is an endoscope system, which comprises an endoscope, the endoscope having at its distal end multiple cameras each having a different field of view (FOV). The system also comprises an image processing box adapted to receive images of different FOVs from the multiple cameras and process the image to form a consolidated image covering 360-degree view of areas surrounding the distal end using the received images of different FOVs and image-stitching techniques.

4 Claims, 46 Drawing Sheets

Four Camera, 125 Degree Lens Image Distortion and Sight Lines

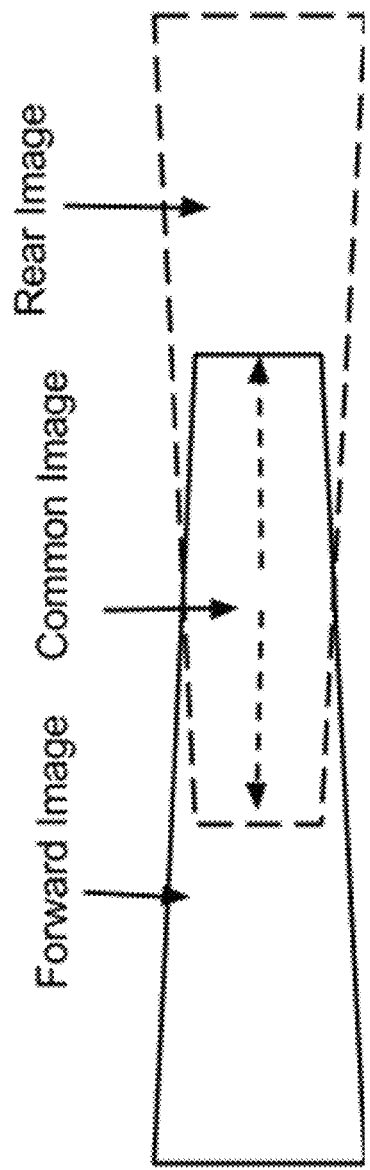
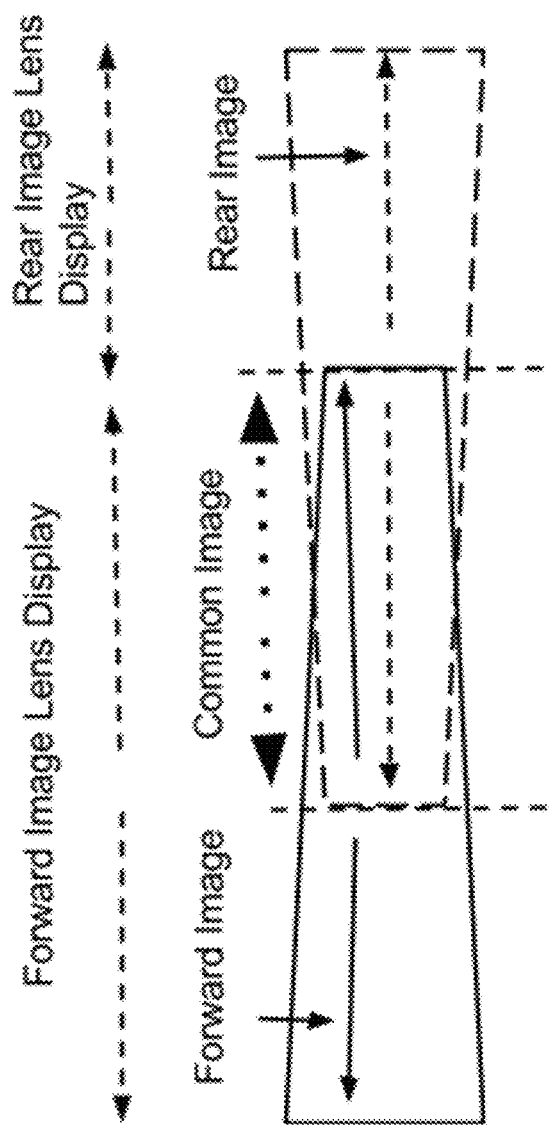
FIG. 3D
FIG. 3E

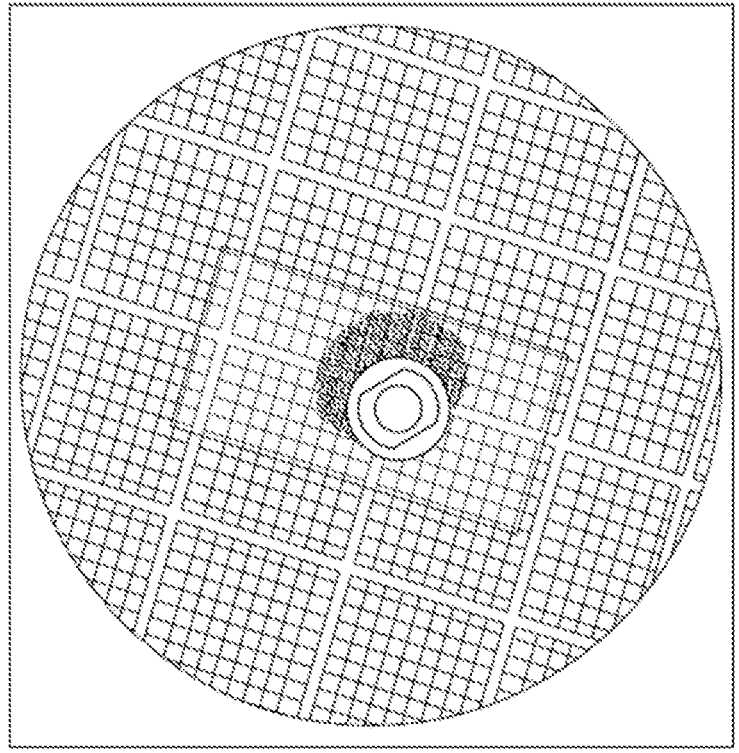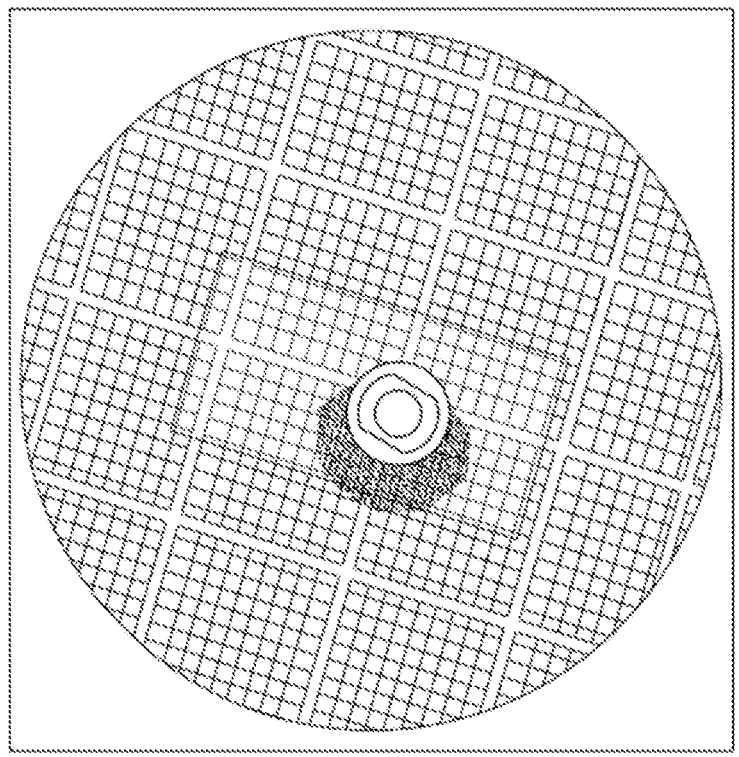
FIG. 5C

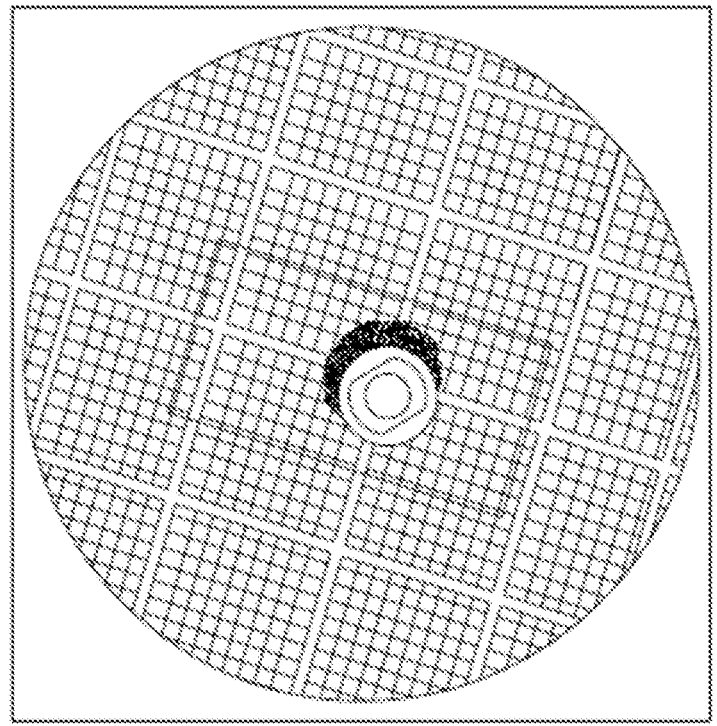
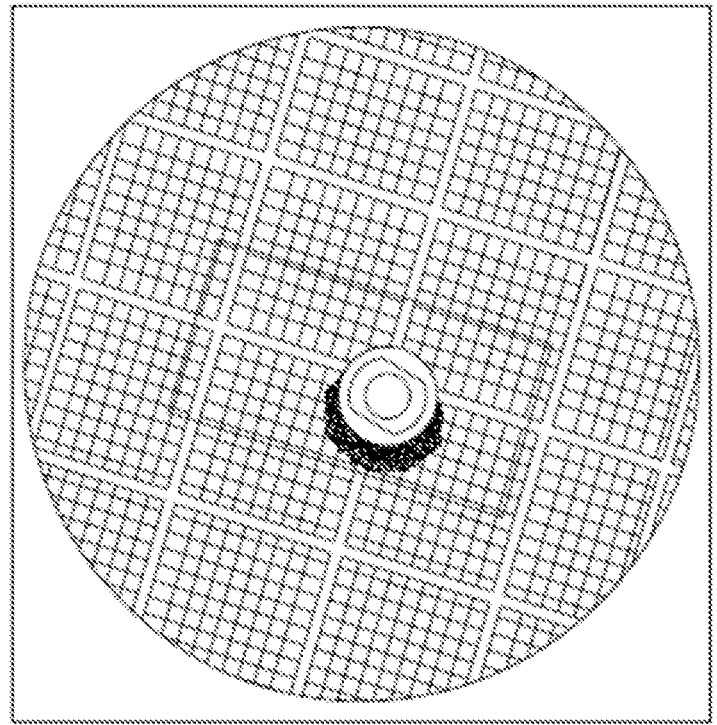
FIG. 5D
Forward facing LED's at 32mm viewing distance, 50% power

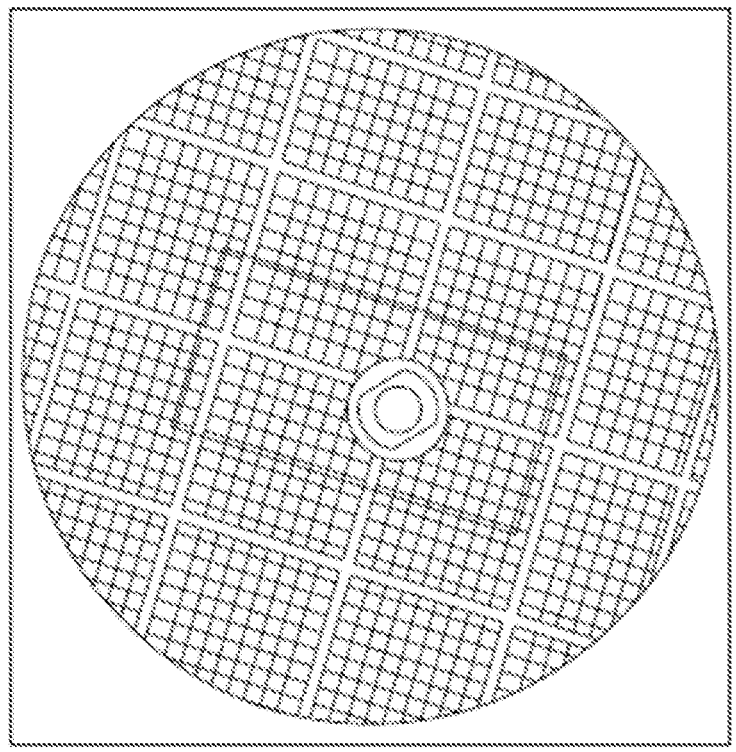
Left LED active
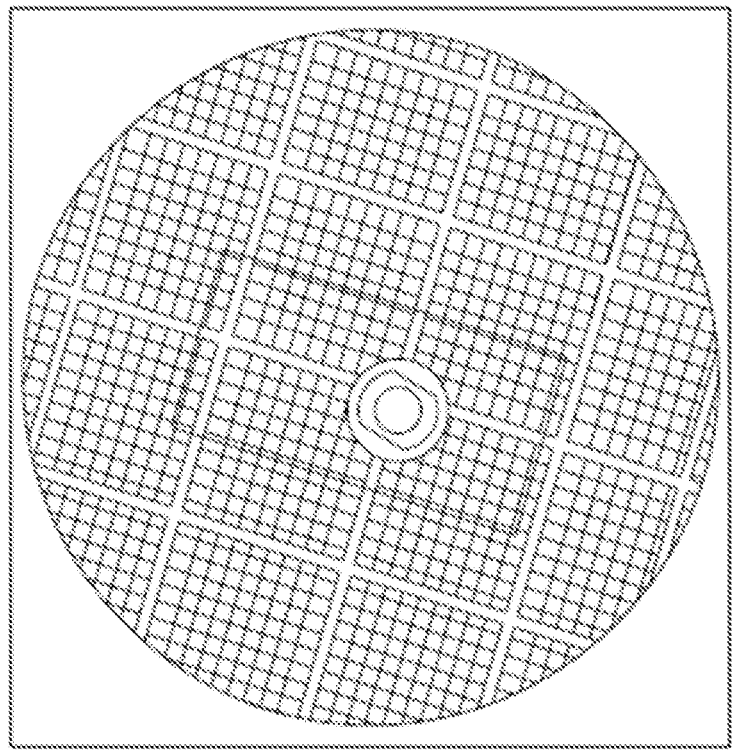
Right LED active
Forward facing LED's at 40mm viewing distance, 50% power
No shadows, LED too far from object and too close to axis of camera to create shadow casting effect
FIG. 5E shadow size related to situation geometry

| Variable | Letter Variable |
|---|---|
| LED Pitch | P |
| Distance to Target | D |
| Height of Target | H |
| Width of Target | W |
| Shadow size | X |

Equation to Represent Relationship
$X = H/D(W/2 + P/2)$

FIG. 5G

Mathematical Proof for relationship

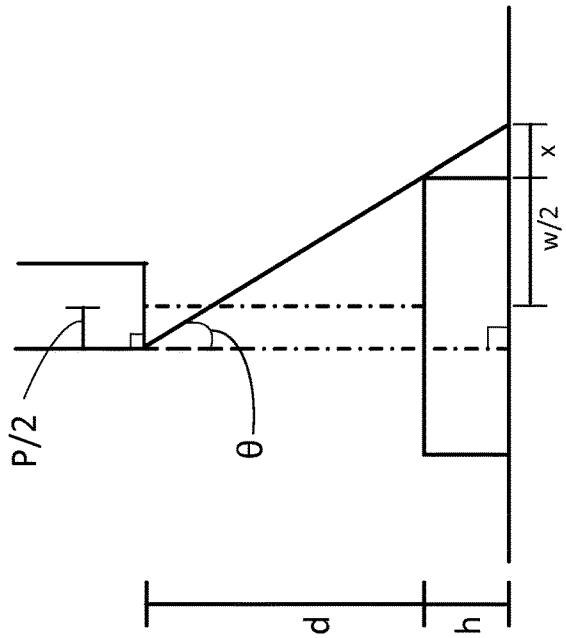

$$\tan(\theta) = \frac{(w/2) + (P/2)}{d}$$

$$\tan(\theta) = \frac{(P/2) + (w/2) + x}{d + h}$$

$$\frac{(w/2) + (P/2)}{d} = \frac{(w/2) + (P/2) + (x)}{d + h}$$

$$(d+h)\left(\frac{w}{2}\right) + (d+h)(P/2) = d\left(\frac{w}{2}\right) + d(P/2) + dx$$

$$d\left(\frac{w}{2}\right) + h\left(\frac{w}{2}\right) + d(P/2) + h(P/2) = d\left(\frac{w}{2}\right) + d(P/2) + dx$$

$$h\left(\frac{w}{2} + \frac{P}{2}\right) = dx$$

$$\boxed{x = \frac{h}{d}\left(\frac{w}{2} + \frac{P}{2}\right)}$$

FIG. 5J

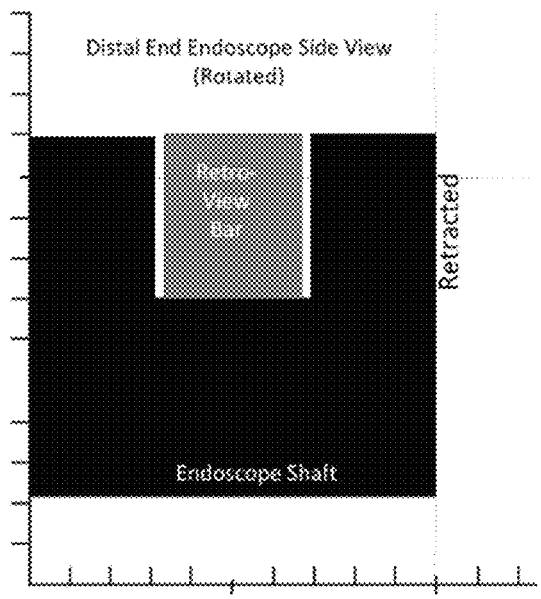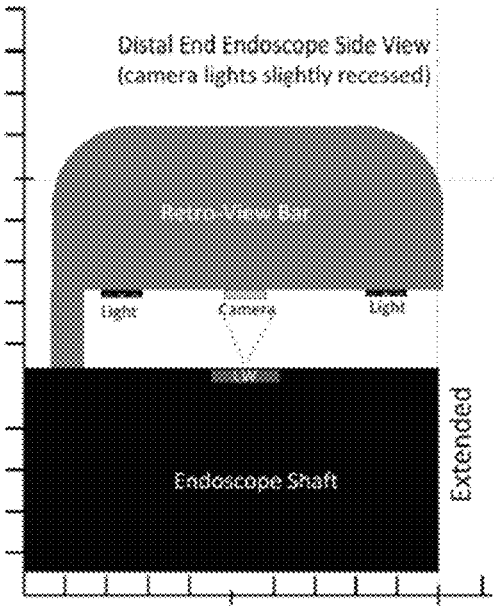
FIG. 7D
FIG. 7E
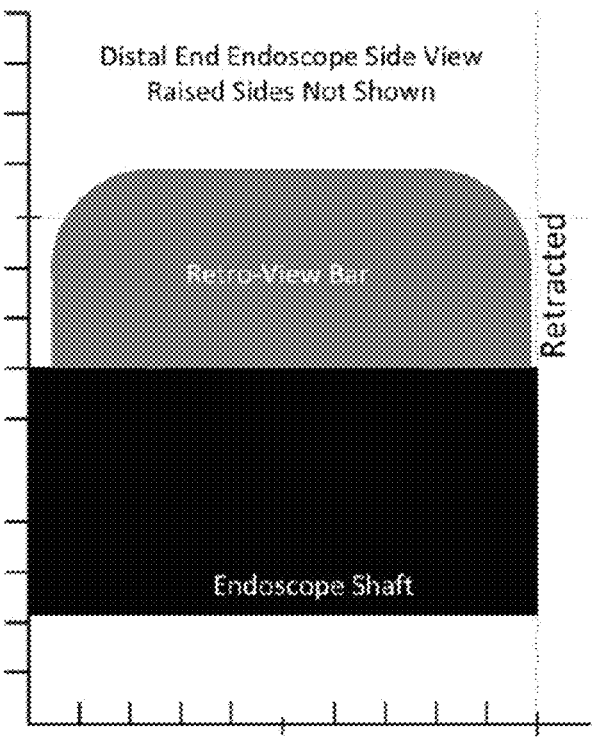
FIG. 7F

INTERCONNECT WIRES FOR USE IN RETROVISION CATHETER

DABURN wire makes appropriate microconductor wire to get out of the catheter

Wiring interconnect to get out with –
- This device require 14 connections with 2 RGB controls and camera. (2xRGB & Gnd) 4 wires camera).
- Can reduce to 9 wires by sharing Left right RGB and putting switch in the common ground.

| Catalog Number | AWG | Strand | Nom. Wall Inches | mm | Nom. O.D. Inches | mm |
|---|---|---|---|---|---|---|
| 2420/28 | 28 | 65/46 | .0035 | 0.089 | 0.022 | 0.559 |
| 2420/29 | 29 | 52/46 | .0035 | 0.089 | 0.020 | 0.508 |
| 2420/30 | 30 | 41/46 | .0035 | 0.089 | 0.019 | 0.483 |
| 2420/31 | 31 | 75/50 | .0035 | 0.089 | 0.017 | 0.432 |
| 2420/32 | 32 | 65/50 | .0035 | 0.089 | 0.016 | 0.406 |
| 2420/33 | 33 | 50/50 | .0035 | 0.089 | 0.015 | 0.381 |
| 2420/34 | 34 | 41/50 | .0035 | 0.089 | 0.014 | 0.356 |
| 2420/36 | 36 | 26/50 | .0035 | 0.089 | 0.013 | 0.330 |
| 2420/38 | 38 | 17/50 | .0035 | 0.089 | 0.012 | 0.305 |
| 2420/40 | 40 | 10/50 | .0035 | 0.089 | 0.011 | 0.279 |
| 2420/42 | 42 | 7/50 | .0035 | 0.089 | 0.010 | 0.254 |

FIG. 8E

DUAL USE CHANNEL WATER AND AIR

Due to limited space in the insertion tube and in the bending area, a double use channel is provided for air and general irrigation.

Single Channel For Air and Irrigation

RGB LIGHTING WITH DUAL SOURCE PER CAMERA-LENS
Lumex SML-LX0404SIUPGUSB tri color LED has size 1mm x 1mm x0.25mm
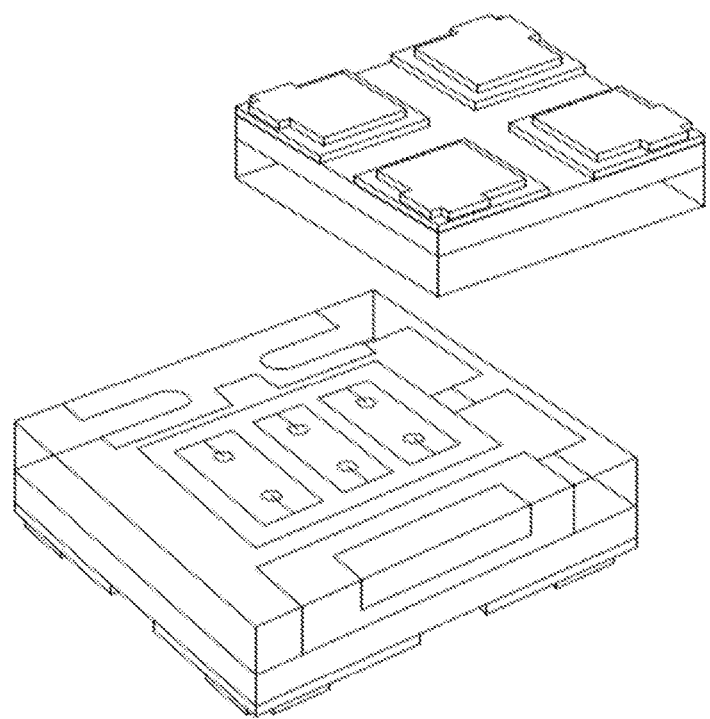
OSRAM LRTBC9TP-CWD5-1+D5E7-25+A, throws more light but is bigger: 3.1mm x 4.5 mm x 0.95mm
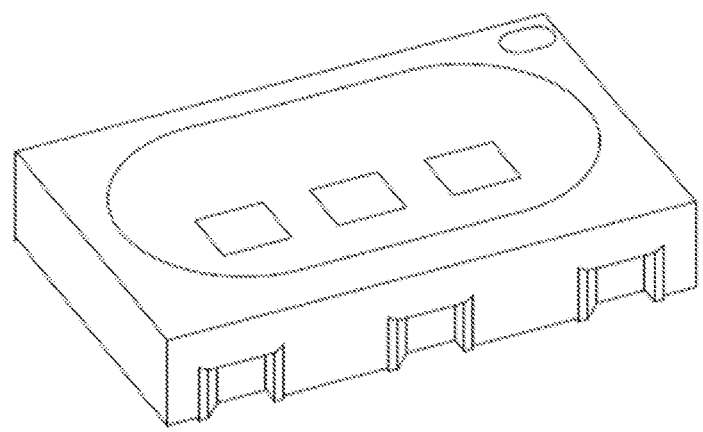
FIG. 11

ENDOSCOPE WITH MULTIPLE VIEWS AND NOVEL CONFIGURATIONS ADAPTED THERETO

CROSS-REFERENCE TO RELATED APPLICATION

This application claims the benefit under 35 U.S.C. § 119(e) of Provisional Patent Application Nos. 62/010,396, 62/117,953, 62/158,513, filed Jun. 10, 2014, Feb. 18, 2015, May 7, 2015, respectively, the entire disclosures of all said prior applications are hereby incorporated by reference.

BACKGROUND

Technical Field

The present disclosure generally relates to an endoscope, and more particularly to an endoscope having multiple cameras capable of capturing multiple simultaneous images of different field of views (FOV) and novel configurations adapted to such an endoscope.

Description of the Related Art

Endoscopes having multiple cameras capable of capturing multiple simultaneous images of different field of views (FOV) have been available during recent years. Such endoscopes, to Applicant's knowledge, still have some deficiencies. The present disclosure is aimed to provide additional advantageous features, particularly features utilizing multiple views of different FOVs, to further improve such endoscopes.

BRIEF SUMMARY

In one aspect, the present disclosure provides, for an endoscope having multiple cameras, a consolidated view of 360-degrees using different images captured from different cameras of different FOVs disposed at, on, and/or adjacent to a distal end of a main shaft of the endoscope.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

BRIEF DESCRIPTION OF THE DRAWINGS

The description of the illustrative embodiments can be read in conjunction with the accompanying figures. It will be appreciated that for simplicity and clarity of illustration, elements illustrated in the figures, unless expressly specified, have not necessarily been drawn to scale. Also, any text and/or any numerical data (numbers) appeared on any drawing figures is provided to illustrate an exemplary embodiment or implementation, and thus is provided for the purpose of illustration and not for the purpose of limitation. For example, the dimensions of some of the elements are exaggerated relative to other elements. Embodiments incorporating teachings of the present disclosure are shown and described with respect to the figures presented herein, in which:

FIGS. 3A-E are pictorials illustrating how known technologies of image stitching are employed to form the exemplary 360-degree consolidated (integrated) views illustrated by FIGS. 2A-I, according to one or more embodiments of the present disclosure.

FIGS. 5A-J are diagrams, graphs or pictorials illustrating a novel so-called "shadow casting" scheme used in connection with an advantageous configuration of a distal end of an endoscope where a set of at least two lights deployed on at least two sides of an adjacent forward view, side view, or rear view camera disposed on, around, or otherwise adjacent to the distal end of the endoscope, according to one or more embodiments of the present disclosure.

FIGS. 7A-G are diagrams, schematics and pictorials illustrating exemplary configurations and implementations of a novel L-shaped rear view (retro-view) catheter (hereinafter simply referred to as L-catheter) used in connection with an endoscope (particularly, a main instrument channel or a dedicated channel of an endoscope) for providing a retrograde view adjacent to a distal end of the endoscope when deployed adjacent thereto, according to one or more embodiments of the present disclosure.

FIGS. 8A-E are diagrams, plan or perspective views, and pictorials, illustrating exemplary configurations and implementations of a novel L-catheter in connection with flex circuit and wiring as related to cameras and lights deployed on the short limb of the L-catheter, according to one or more embodiments of the present disclosure.

FIG. 11 is a pictorial illustrating exemplary LEDs relating to a disclosed novel use of LEDs to provide lighting for one or more cameras used in connection with, e.g., a rear view catheter (such as an L-catheter) deployed adjacent to a distal end of an endoscope, or an endoscope having multiple simultaneous views of different FOVs, according to one or more embodiments of the present disclosure.

DETAILED DESCRIPTION

Figure 1A:
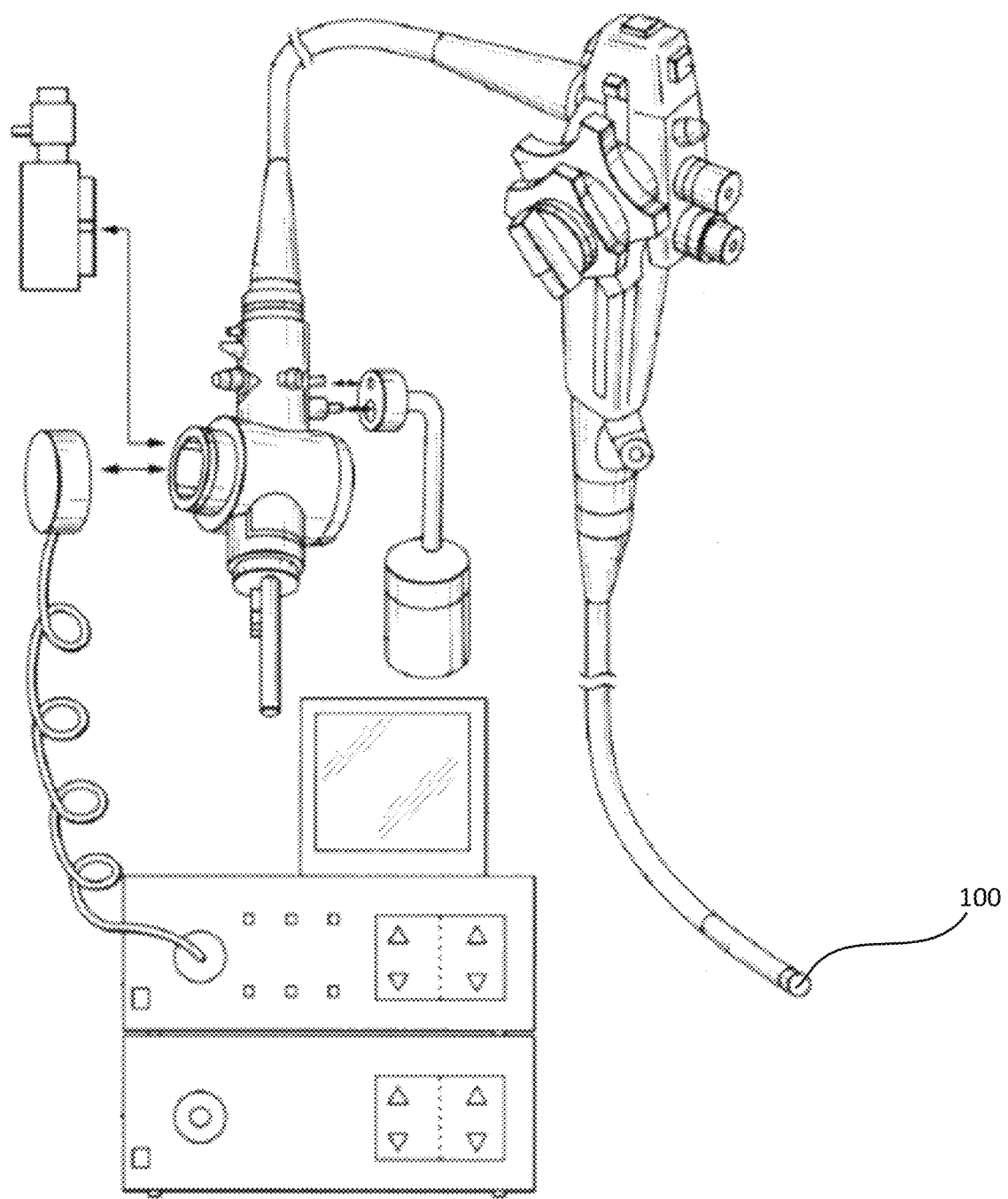
FIGS. 1A-C are perspective views illustrating an exemplary endoscope, an exemplary configuration of a distal end of an endoscope with a forward view camera (lens), and an exemplary configuration of a distal end of an endoscope having multiple cameras disposed around or adjacent to the distal end each having a different field of view (FOV), in accordance with the context of the present disclosure.

In the following detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. Moreover, the use of the terms first, second, etc. do not denote any order or importance, but rather the terms first, second, etc. are used to distinguish one element from another.

Those of ordinary skill in the art will appreciate that the circuit components and basic configuration depicted in the following figures may vary. Other circuit components may be used in addition to or in place of the components depicted. The depicted example is not meant to imply architectural or other limitations with respect to the presently described one or more embodiments and/or the general disclosure.

Within the descriptions of the different views of the figures, the use of the same reference numerals and/or symbols in different drawings indicates identical, similar, or closely related items, and similar or closely related elements can be provided similar names, reference numerals, and reference alpha-numerals throughout the figures. If a reference numeral is once used to refer to a plurality of like elements, unless required otherwise by context, the reference numeral may refer to any, a subset of, or all of, the like elements in the figures bearing that reference numeral. A reference alpha-numeral may refer to one implementation or one portion of one element or a plurality of like elements bearing the same base reference numeral. The specific identifiers/names, reference numerals and reference alpha-numerals assigned to the elements are provided solely to aid in the description and are not meant to imply any limitations (structural or functional or otherwise) on the described embodiments.

In the description, relative terms such as "left," "right," "vertical," "horizontal," "upper," "lower," "top" and "bottom" as well as any derivatives thereof should be construed to refer to the logical orientation as then described or as shown in the drawing figure under discussion. These relative terms are for convenience of description and are not intended to convey any limitation with regard to a particular orientation.

Figure 1B:
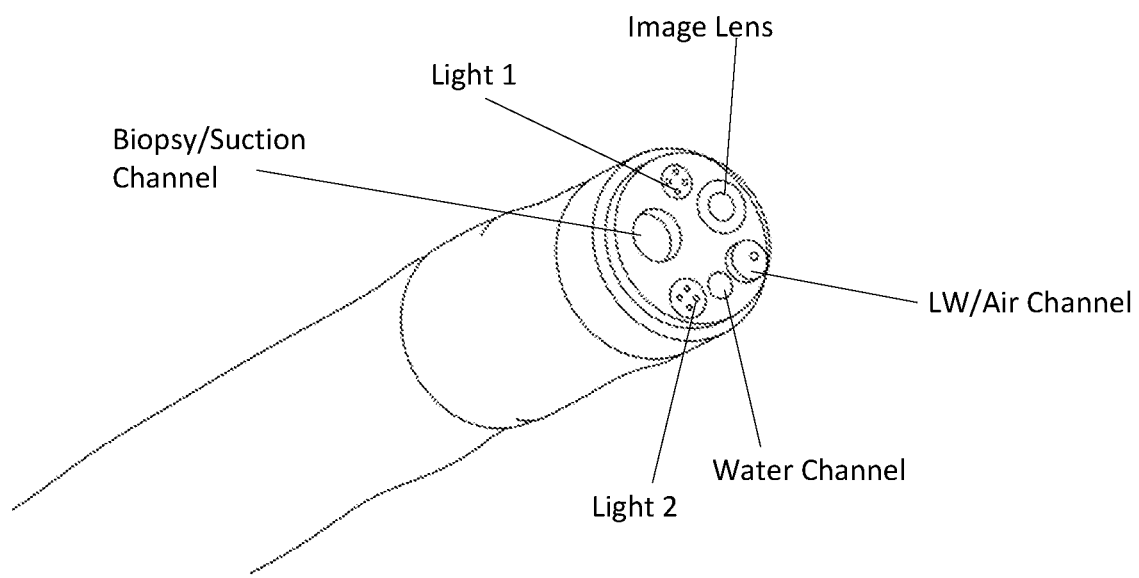
Figure 1C:
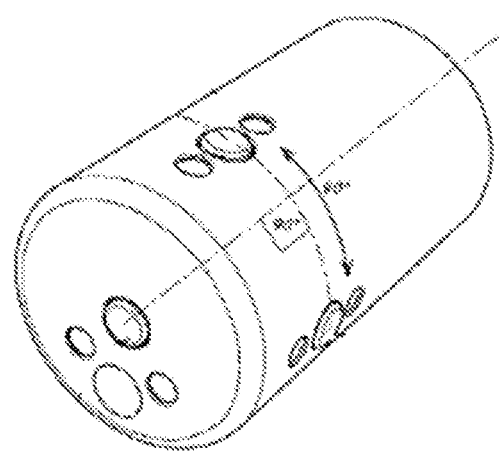

With reference now to the figures, and beginning with FIGS. 1A-C, there are perspective views illustrating an exemplary endoscope with a distal end 100 of its main shaft. Specifically, FIG. 1A shows what a typical endoscope looks like, including distal end 100 of an endoscope's main shaft, which is most relevant to the present disclosure.

FIG. 1B illustrates an exemplary configuration of distal end 100 of an endoscope, which may be implemented in the form a contraption (hereinafter also referred to as "distal end contraption" and also assigned to reference numeral 100). Hereinafter, the term "distal end" and "distal end contraption" may be used interchangeably to refer to one or more configurations and implementations of the distal end. As shown, distal end contraption 100 may comprise or otherwise be equipped with, a forward view camera (lens), multiple lights, a biopsy/suction channel (which, for the purpose of the present disclosure, would be hereinafter also referred to as a "main instrument channel"), and a Lens-Wash (LW) channel (which, for the purpose of the present disclosure, would be hereinafter also referred to as an "air/water channel"). FIG. 1C illustrates a distal end 100 of an endoscope having multiple cameras deployed on or adjacent to distal end 100 and being capable of simultaneously capturing images of different FOVs, including forward view images (by a forward-view camera), side view images (by, e.g., a side-pointing camera), and rear view images (by, e.g., a rear view catheter). Applicant's U.S. Pat. No. 8,585,584, titled "Dual View Endoscope", describes such a multi-view endoscope with simultaneous forward and rear views, whose entire disclosure is hereby incorporated by reference. U.S. Patent Application Publication No. 2014/048644, titled "Multi-Element Cover for a Multi-Camera Endoscope" also describes, inter alia, such a multi-view endoscope with simultaneous forward and side/rear views, whose entire disclosure is also hereby incorporated by reference.

As used herein, each of the terms "forward", "side", or "rear", when used in conjunction with the term "view" and/or "camera", is only used to refer to a direction to which the lens of its associated image-capturing camera points to relative to the longitudinal axis of a main shaft of an endoscope, and is not with respect to direction of a coverage by the FOV of the associated lens relative to the direction of the coverage of the FOV of a main front view camera. Thus, a "side-view" camera may capture a "rearview" or "rear view" as part of its FOV in relation to the forward direction which a forward view camera points to, when the FOV of the "side-view" camera includes or otherwise covers an acute angle to the longitudinal axis in a rearward direction pointing from the distal end of the main shaft to a proximal end of the main shaft.

Figure 9A:
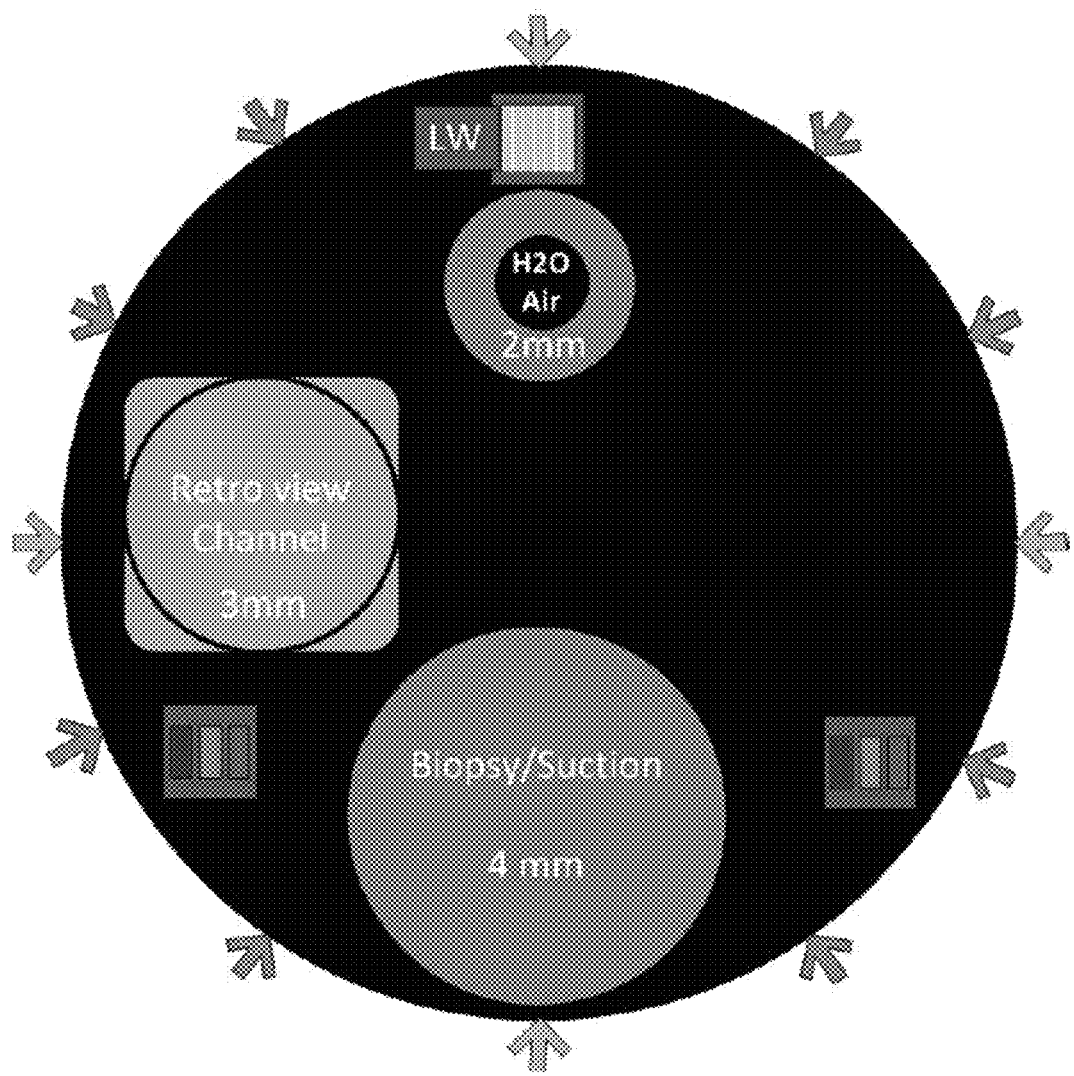
FIGS. 9A-B are plan views or pictorials illustrating exemplary novel configurations of one or more side-view cameras deployed or otherwise disposed adjacent to the distal end of the endoscope on the periphery of the main shaft of the endoscope (with the lens of the camera facing or pointing to a side of the main shaft) in conjunction with a dedicated channel for rear view catheter, according to one or more embodiments of the present disclosure.
Figure 9B:
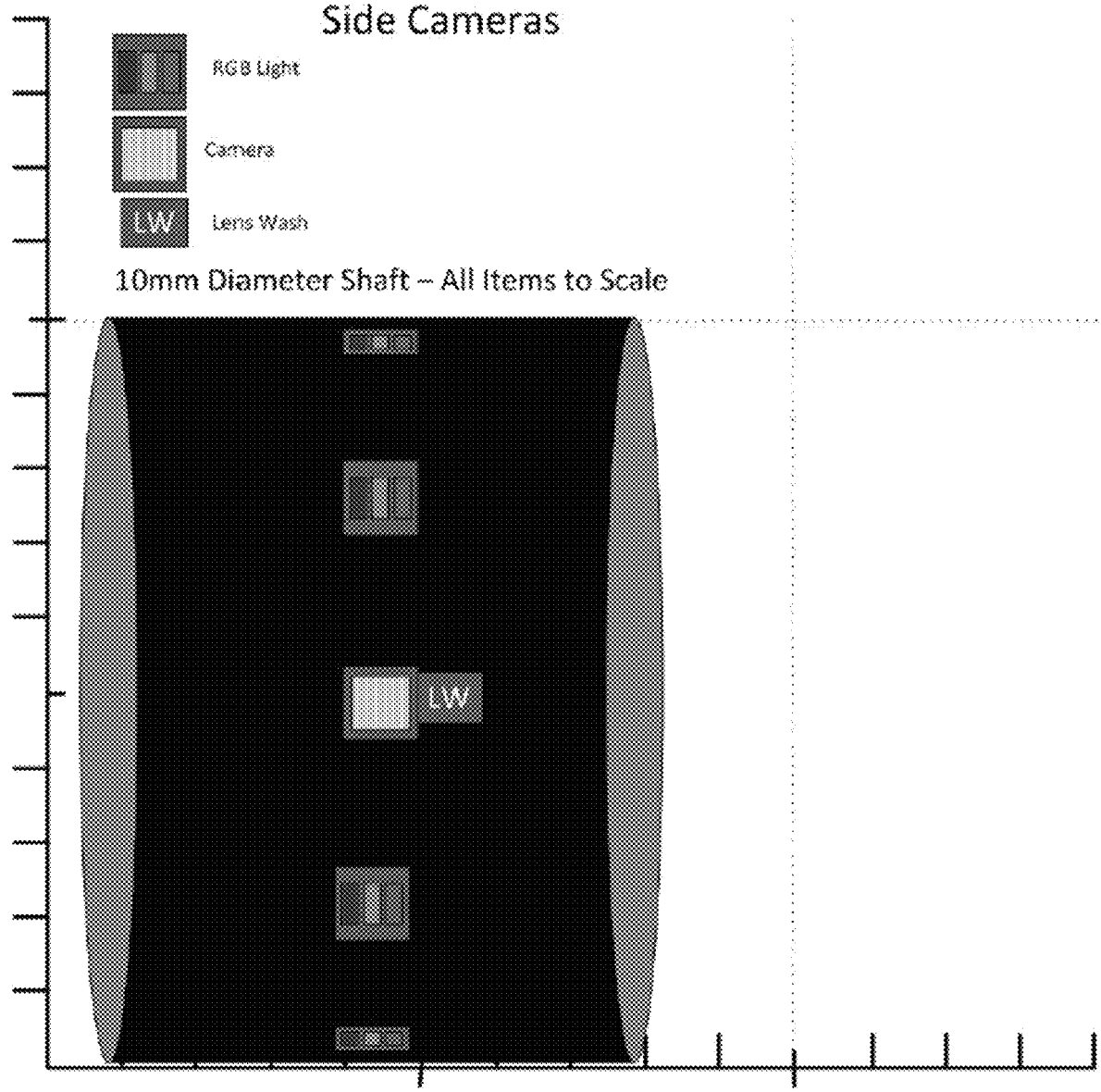

According to one aspect of the present disclosure, a rear view catheter can be used in conjunction with any known endoscope comprising one or more side rear view modules. FIGS. 9A-B illustrate exemplary novel configurations of a side-view camera deployed or otherwise disposed adjacent to the distal end of the endoscope on the periphery of the main shaft of the endoscope (with the lens of the camera facing or pointing to a side of the main shaft) in conjunction with a dedicated channel for a rear view catheter, according to one or more embodiments of the present disclosure. As illustrated in FIGS. 9A-B, in one embodiment, the parent endoscope (with respect to the rear view catheter) comprises a dedicated rear view channel traversing through the length of the shaft and having a proximal end and a distal end 100, in addition to an instrument channel traversing through the length of the shaft and having a distal end and a proximal end.

FIGS. 2A-I are diagrams, schematics and pictorials of exemplary integrated views collectively illustrating exemplary novel configurations of an consolidated view, in which a 360-degree view of areas surrounding distal end 100 is achieved through multiple images captured by multiple cameras deployed or otherwise provided around or adjacent to distal end 100.

Figure 2A:
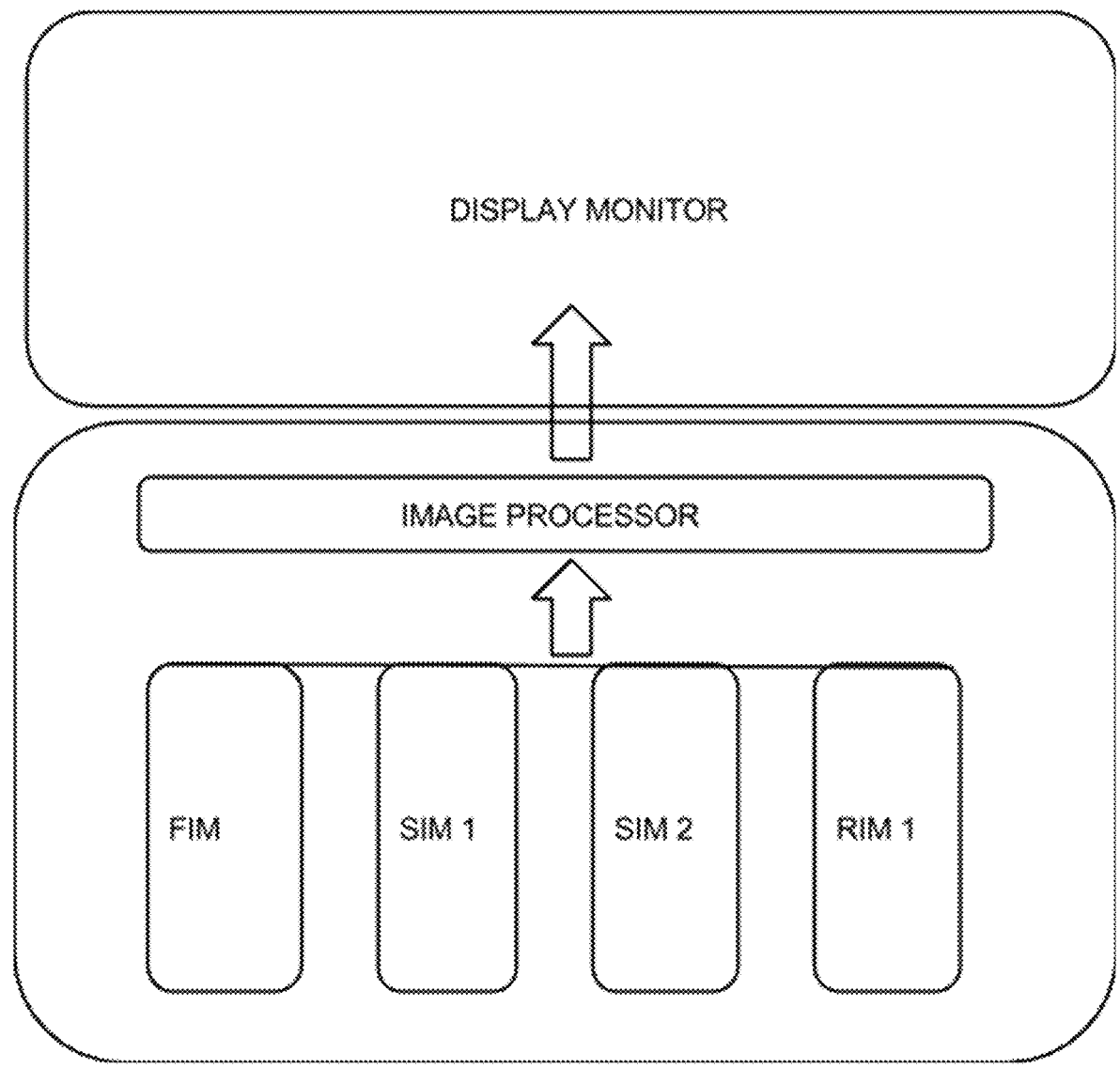
FIGS. 2A-I are diagrams, schematics and pictorials collectively illustrating exemplary novel configurations of a consolidated view, in which a 360-degree view of areas surrounding a distal end of an endoscope is achieved through processing and positioning multiple images captured by multiple cameras deployed or otherwise provided around or adjacent to the distal end within a pre-set configuration or framework used for forming a consolidated view, according to one or more embodiments of the present disclosure.

Referring to FIG. 2A, in one embodiment, a multi-view endoscope and a rear view catheter are operatively connected to a single processor box comprising of an image processor, power source and light source (optional).

Relatedly, as will be disclosed below, use of LED bulbs in a rear view catheter would obviate the need for light source, as the LED bulbs would be connected to a power source and provide direct illumination of a hollow organ (into which distal end 100 is inserted). The advantage of this preferred embodiment is that it obviates the need for a light guide and light source, and makes a rear view catheter thinner and more flexible and simpler to use.

Same may be true when LED bulbs are used in place of light guide and light source in a disclosed endoscope, which is the case in one embodiment of an endoscope of the present disclosure. In one embodiment, a single transmission cable connects the endoscope to a single processor box. The transmission cable contains the following: i) electric cables connection the LED lights of the parent endoscope to power source; ii) electric cables connecting the image lenses of the disclosed endoscope to the circuitry of the image processor; and iii) electric cables from the female receptacle to the processor box. In one implementation, the processor box also contains an air/water pump to push air/water into the air/water channel of the disclosed endoscope.

Figure 2B:
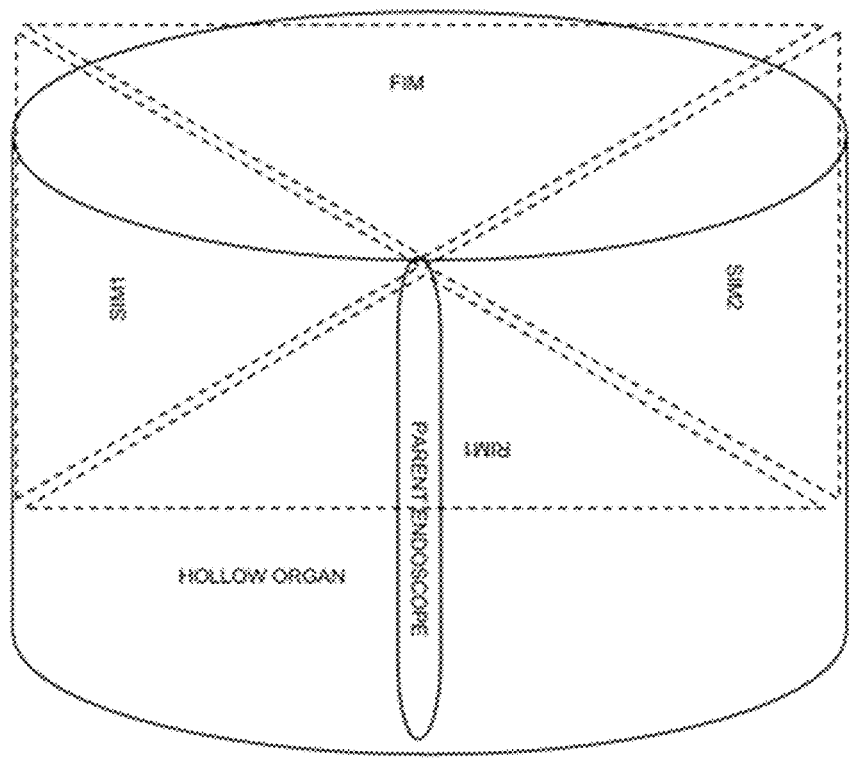
Figure 2C:
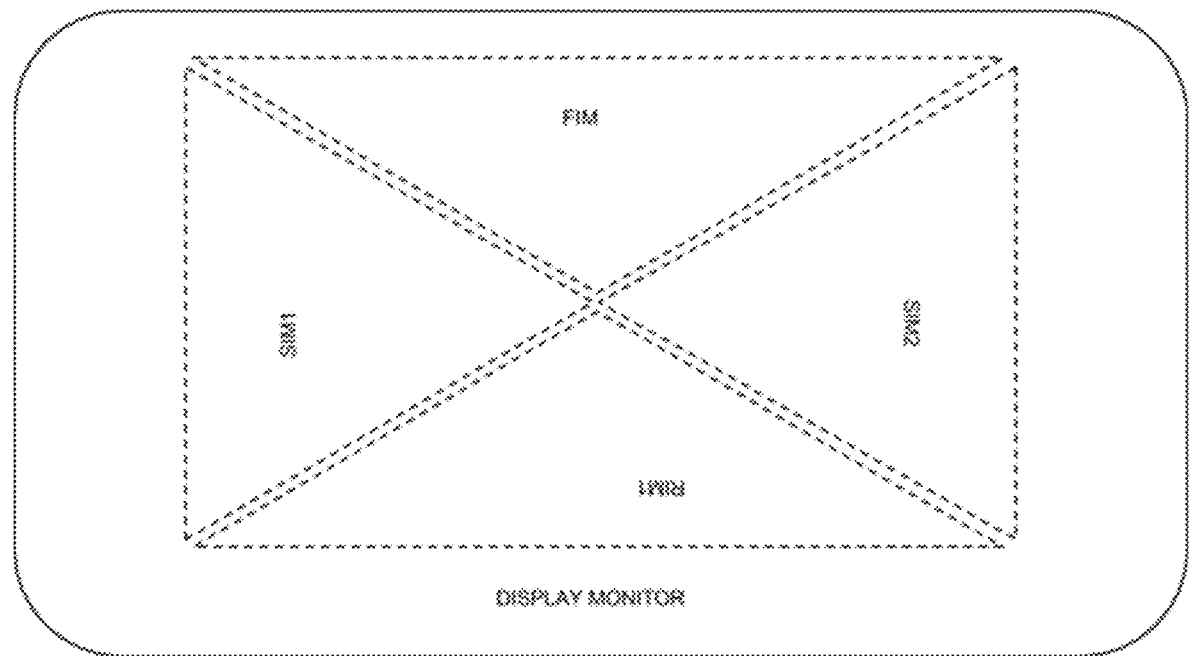
Figure 2D:
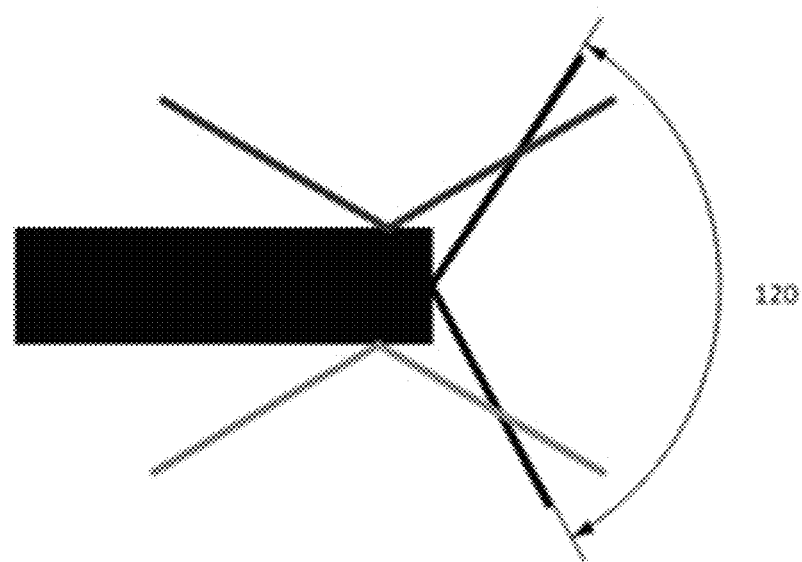
Figure 2E:
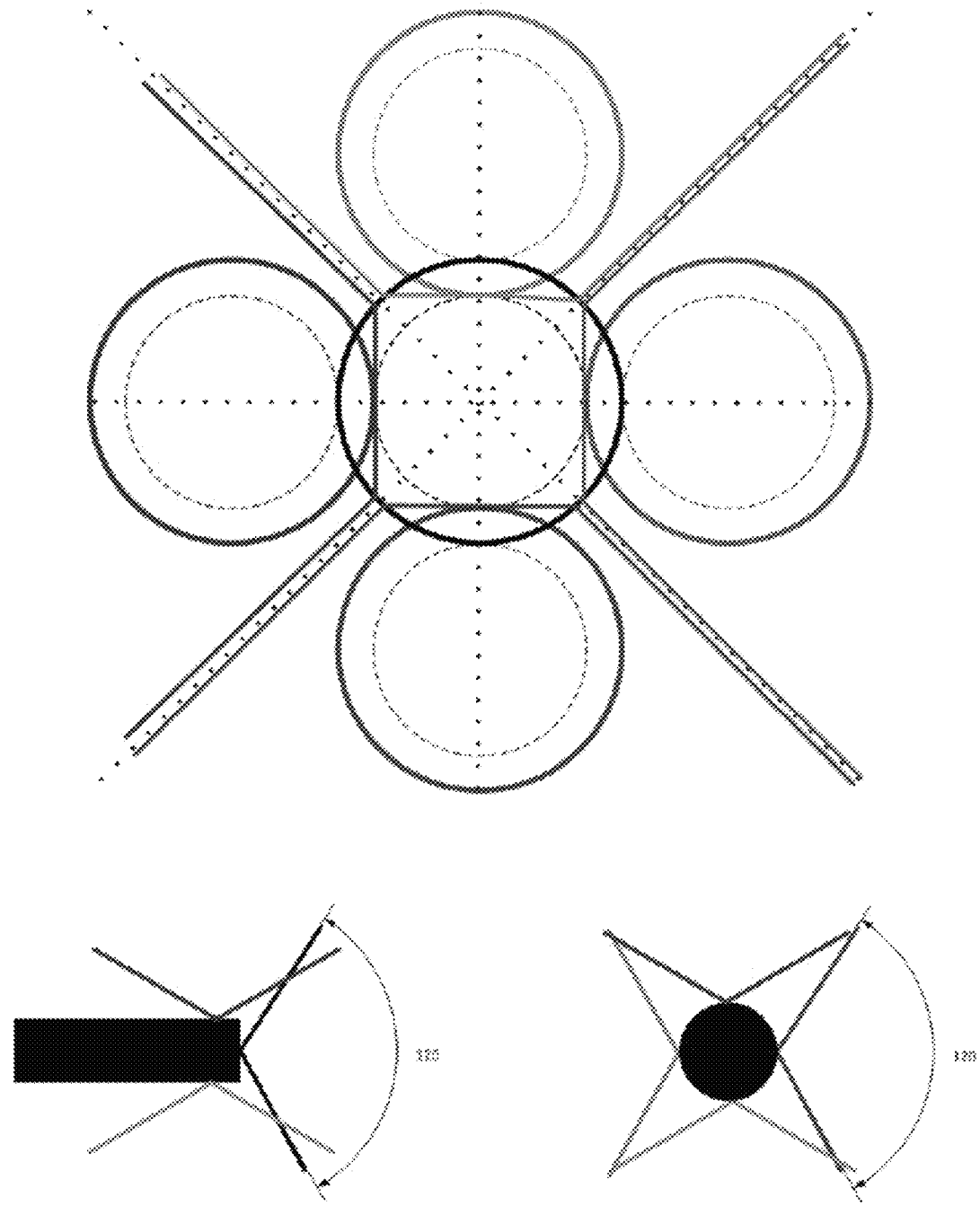
Figure 2F:
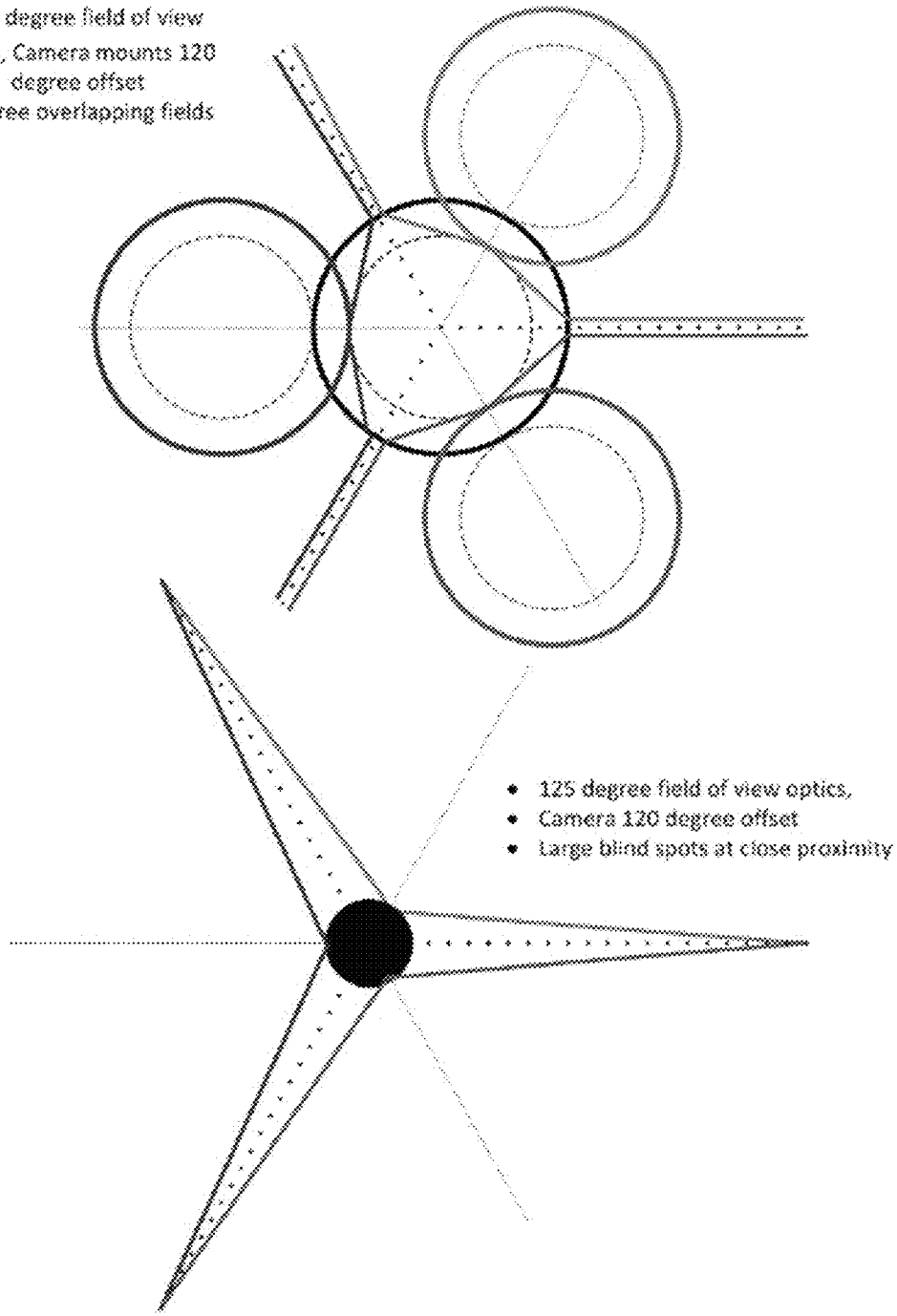
Figure 2G:
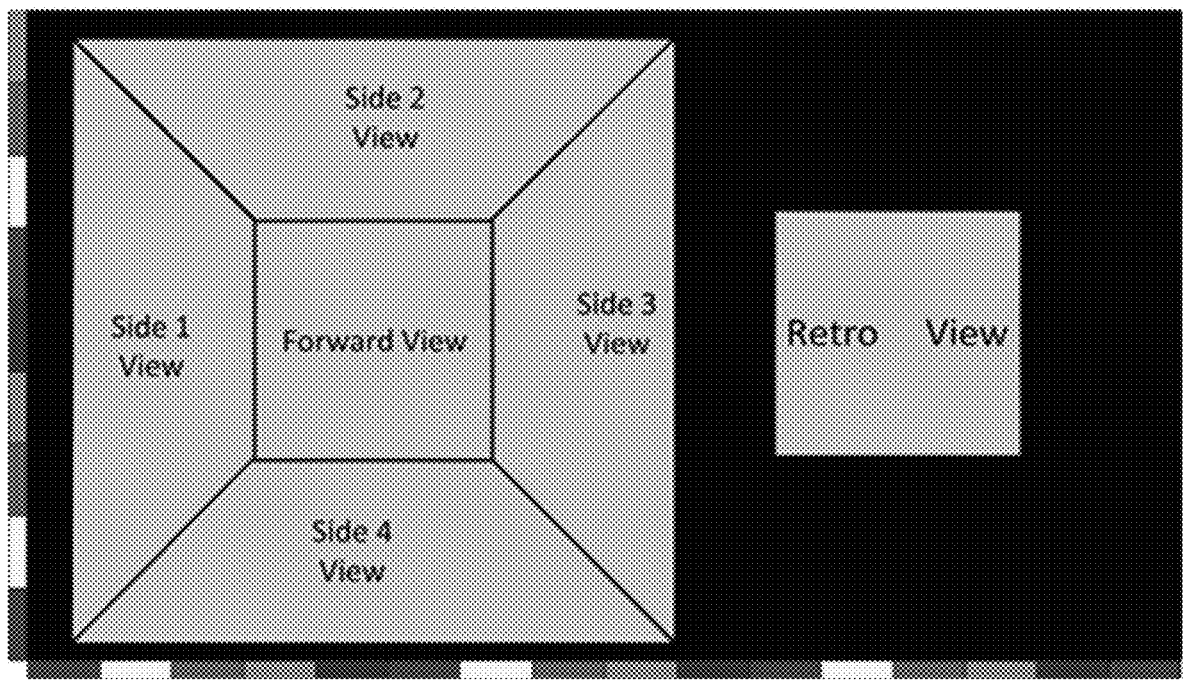
Figure 2H:
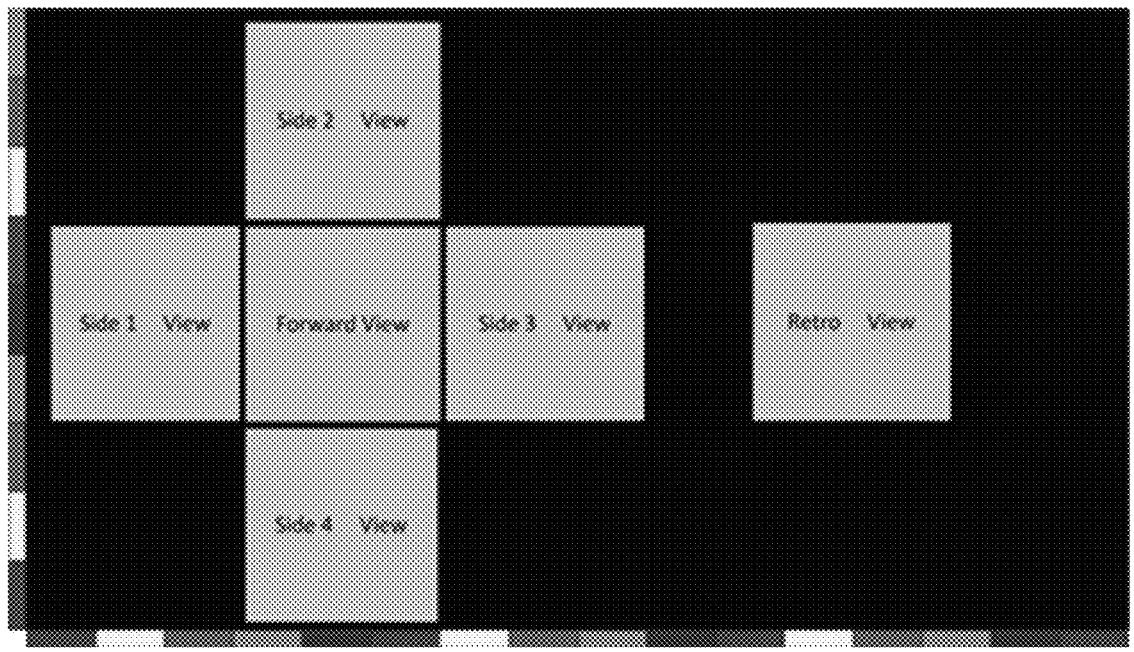
Figure 2I:
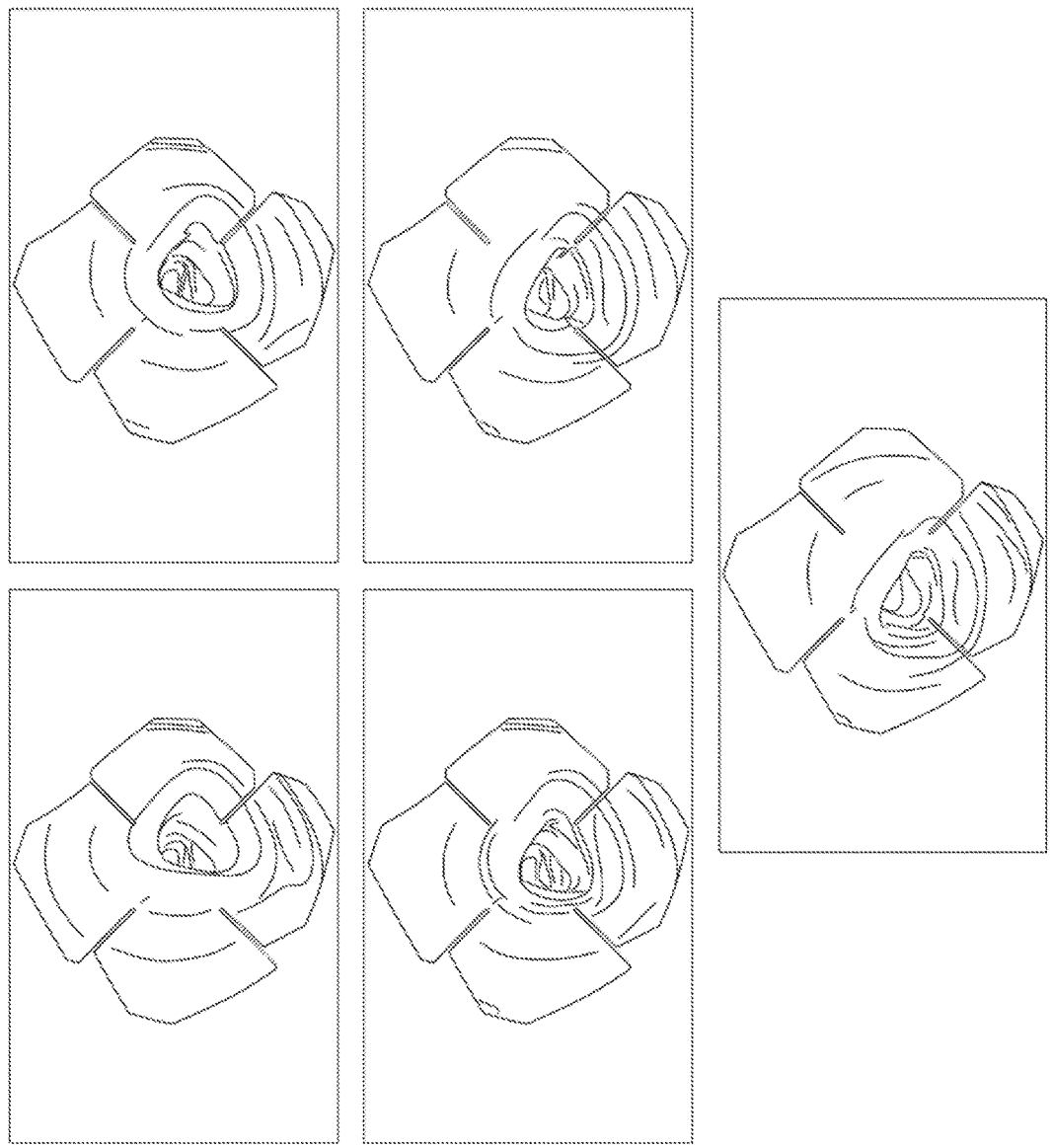
Figure 3A:
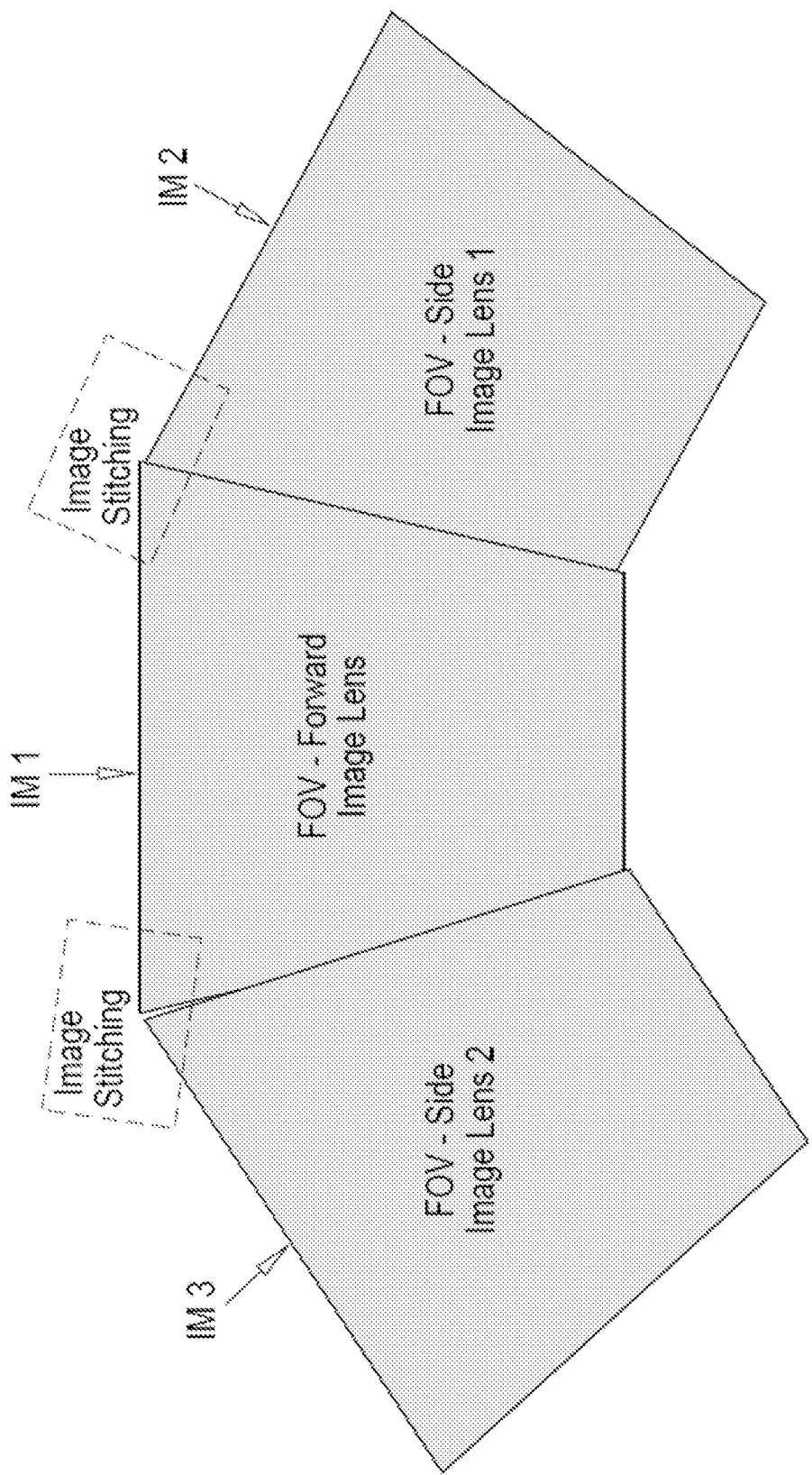
Figure 3B:
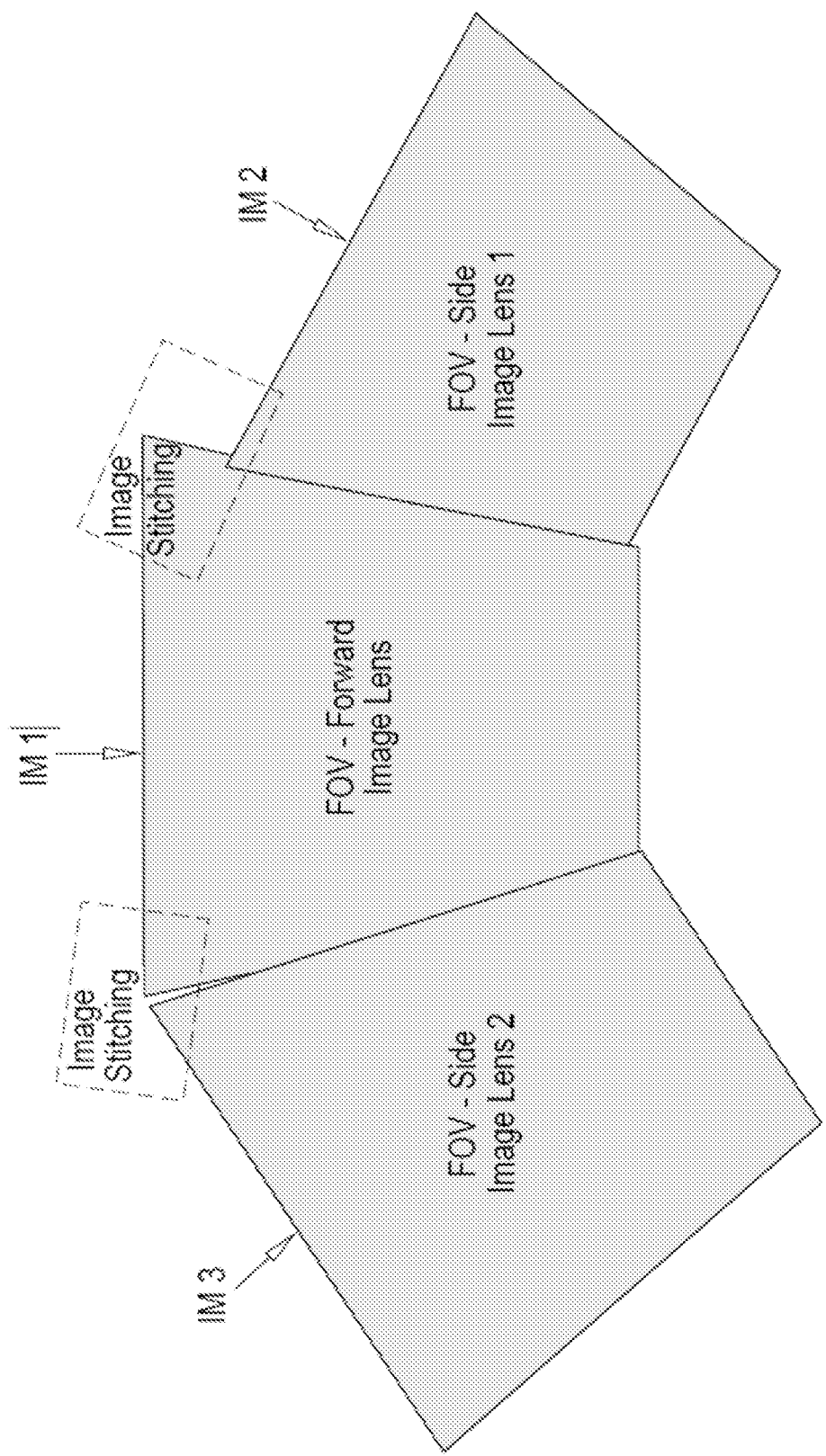
Figure 3C:
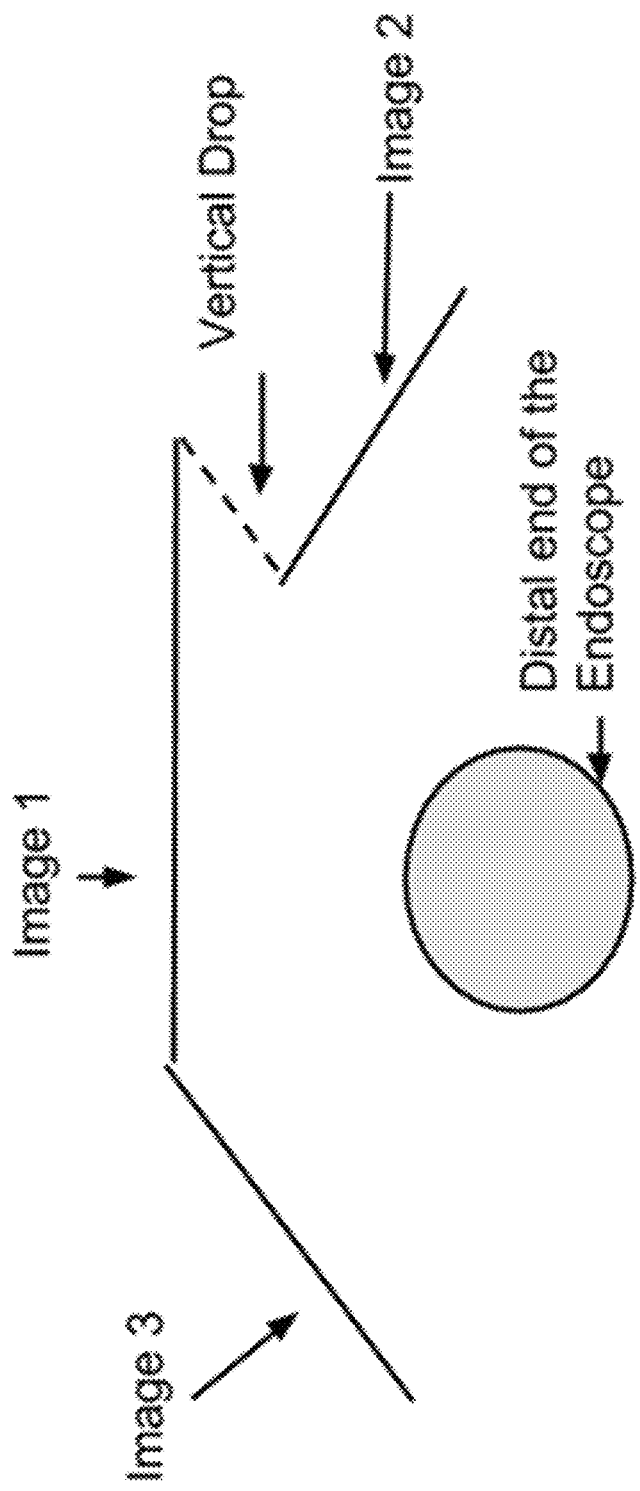

FIGS. 2B-C illustrate an exemplary configuration of a consolidated 360-degree view with respect to views captured by a forward view camera, two side view cameras, and a rear view camera. FIGS. 2D-E illustrate another exemplary configuration of a consolidated 360-degree view with respect to images captured by a forward view camera and four side view cameras. FIG. 2F illustrates another exemplary configuration of a consolidated 360-degree view with respect to images captured by a forward view camera and three periphery (side) view cameras. FIGS. 2G-H illustrate another exemplary configuration of a consolidated 360-degree view with respect to images captured by a forward view camera, four side view cameras, and an optional rear view camera. FIG. 2I shows examples of a resulting consolidated image of 360-degree view with respect to images captured by a forward view camera, four side view cameras, using the pre-set configuration illustrated in FIG. 2G (without the retro-view).

Image Consolidation & Stitching:

Referring to FIGS. 2B and 2C, images from multiple images lenses are consolidated, which may be consolidated into one composite consolidated image for viewing on a display monitor. However, more than one consolidated images may be obtained and should not be considered limiting the scope of the present disclosure. One method of image consolidation is disclosed in one of Applicant's earlier US applications (namely, U.S. Patent App. Pub. No. 2011/0160530), the entire disclosure of which is herein incorporated by reference. The front and the side image lenses are strategically placed at the distal end and the shaft of the endoscope such that there is minimal or no overlap between the FOVs of two corresponding adjacent image lenses. Additionally two corresponding and adjacent image lenses are strategically placed at the distal end and/or the shaft of the endoscope such that the margins of the field of view of the two adjacent image lenses closely juxtapose and approximate each other such that when the two images from two adjacent image lenses are stitched together, they appear, as close as possible, as one continuous and composite image from adjacent areas of the hollow organ. This is accomplished by determining the field of view (FOV) of each image lens and placing an image lens at the margin of the FOV of the corresponding preceding image lens.

Once two images from two adjacent and corresponding image lenses are received in the image processor, an image management software stitches the two images. The software is programmed to stitch the two adjacent images along a corresponding axis in order to provide a continuous and composite image comprising of two images from the two adjacent image lenses.

Referring to FIGS. 3A-E, the two images from adjacent image lenses are stitched along their respective 'Y' axis and the resulting image is a continuous and composite image of the hollow organ under the field of view of the two adjacent and corresponding image lenses. The software is also programmed to recognize usual patterns, differences in depth of vision, and common deviations thereof, along the common axis of the two images. When the software finds recognized deviations in patterns and/or depth of vision along the common axis of the two images to be stitched together, it is corrected and/or compensated by the software before the two images are stitched together and the resulting image is a continuous and composite image of the hollow organ under the field of view of the two adjacent and corresponding image lenses. The image processing software is also programmed with baseline angular separation between the two adjacent and corresponding image lenses and thereafter detects and incorporates any deviation from the baseline angular separation between the two image lenses into the composite image, such that deviation of angle of separation is visible on the composite image.

Referring to FIGS. 3D and 3E, in the case of the rear view catheter, the image processing software is programmed to, e.g., discard the images in the FOV of the rear view catheter that is already covered in the FOV of the front and/or side image lenses and stitch only the images in the FOV of the rear view catheter that is exclusive to the rear view catheter. Having said that, the images obtained from the rear view catheter can be displayed separately from the front and side image lenses integral to the shaft of the endoscope, either on the same display monitor or on a separate display monitor.

Applicant would like to note that although technologies of image stitching has been well known, image stitching technologies, however, have NEVER been used to create or otherwise form a consolidated view of a pre-set configuration, such as those shown in FIGS. 2B-2H, in connection with a multi-view endoscope illustrated in, e.g., FIG. 1C or described in the incorporated U.S. Patent Application Publication No. 2014/048644.

Field Display of Each Image Lens to Locate Abnormal Lesion

Figure 4A:
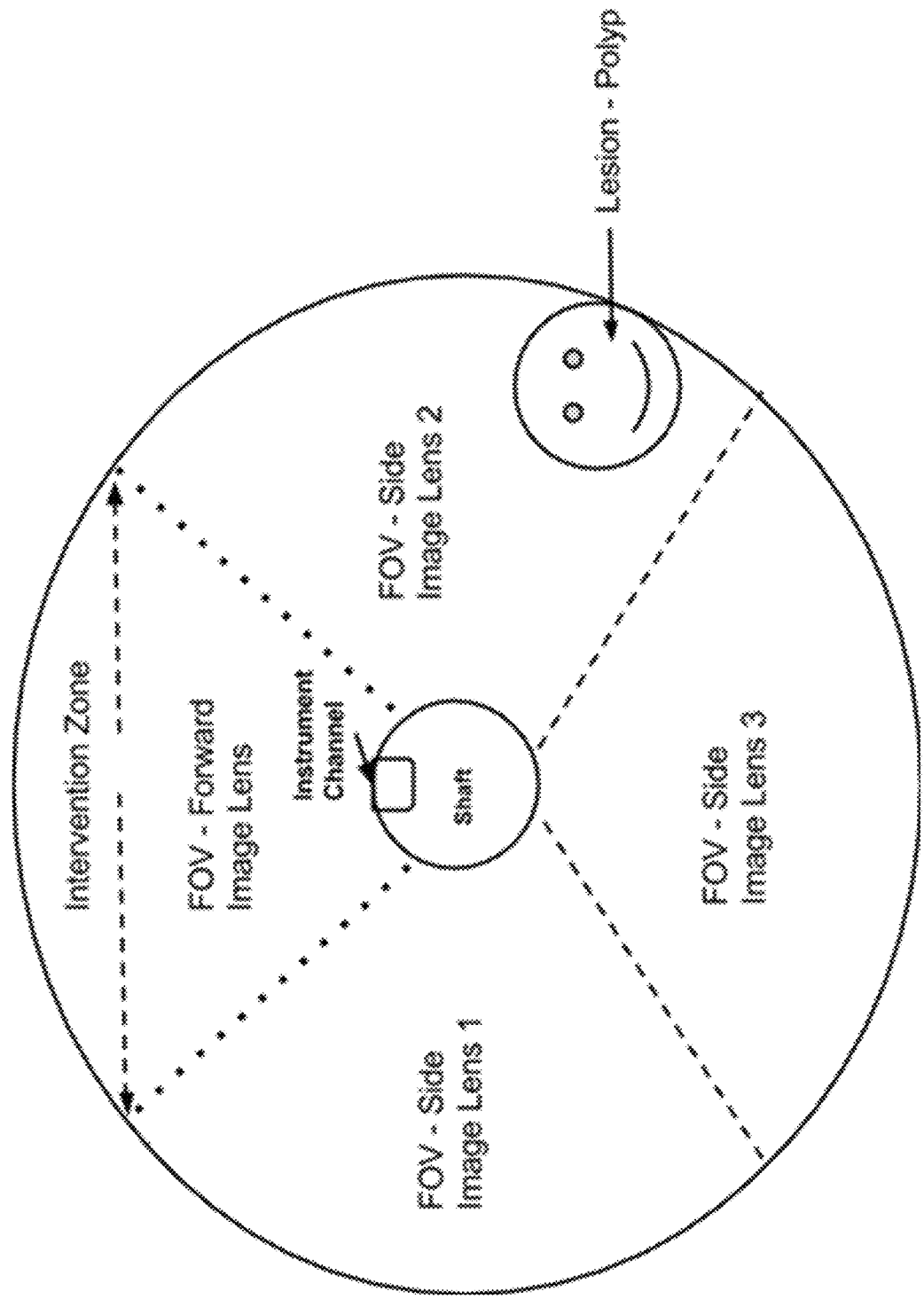
FIGS. 4A-B are pictorials illustrating how an exemplary 360-degree consolidated view of a pre-set configuration (as illustrated in FIGS. 2A-I) in regards to a set of pre-set multiple cameras deployed or otherwise disposed around or adjacent to the distal end (with each camera having a different FOV), can use the FOV of a preset such camera as a marker to mark the location and orientation of a lesion or polyp discovered therein relative to, e.g., a forward of FOV of a participating forward view camera covering a so-called "intervention zone", thus greatly facilitating the operator of the endoscope (such as an endoscopist) to decide as to how the distal end should be turned so that the discovered lesion or polyp falls within the "invention zone", according to one or more embodiments of the present disclosure.
Figure 4B:
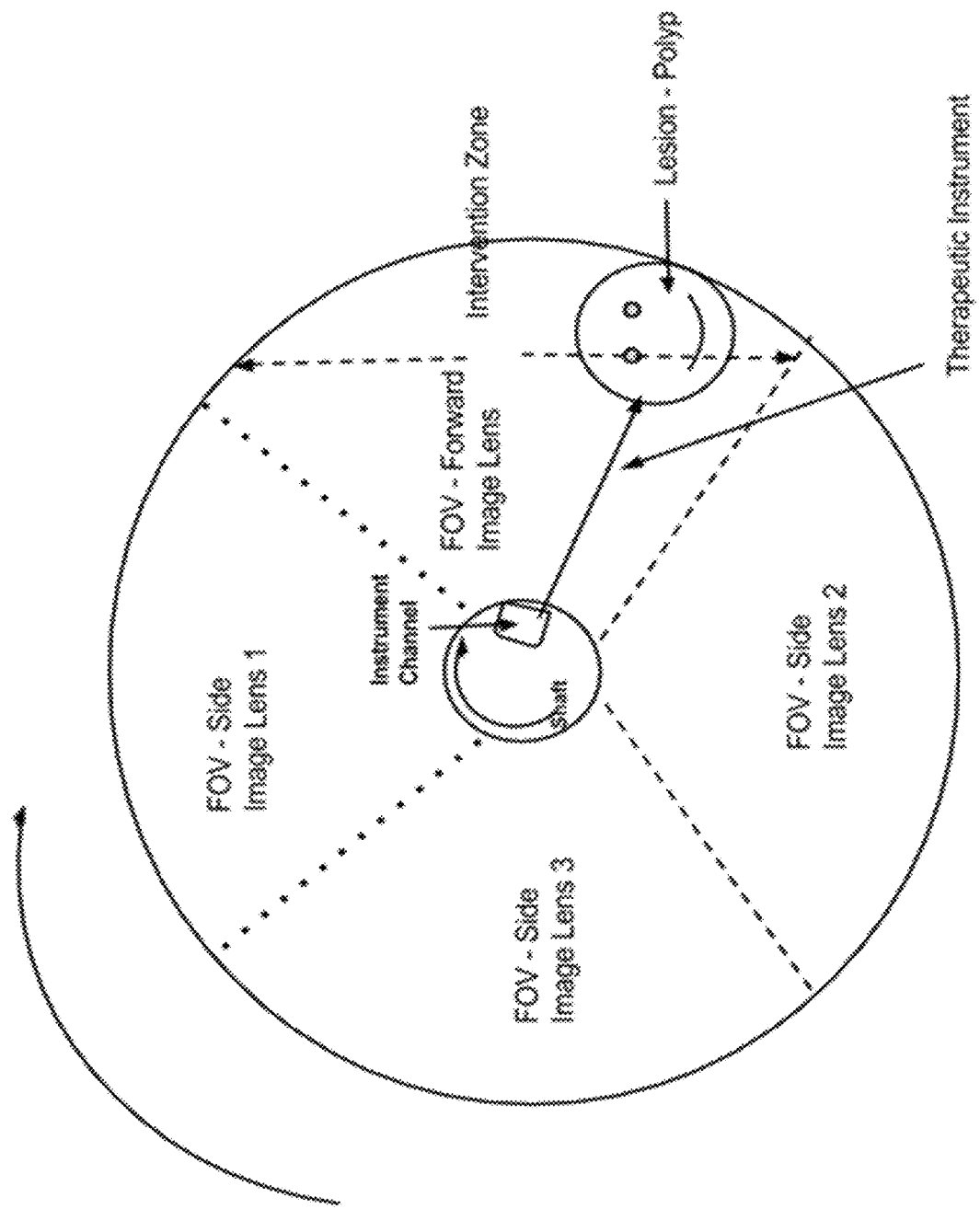

FIGS. 4A-B are pictorials illustrating how an exemplary 360-degree consolidated view of a pre-set configuration (as illustrated in FIGS. 2A-I) in regards to a set of multiple cameras deployed or otherwise provided around or adjacent to the distal end (with each camera having a different FOV), can use a participating FOV as a marker to mark the location and orientation of a lesion or polyp discovered therein relative to a participating forward FOV covering a so-called "intervention zone", thus greatly facilitating the operator of the endoscope (such as a physician doctor) how the distal end should be turned so that the discovered lesion or polyp falls within the "invention zone", according to one or more embodiments of the present disclosure.

A skilled artisan readily appreciates that this FOV marker scheme ONLY becomes available and feasible when a consolidated view similar to, e.g., a 360-degree consolidated view of pre-set configurations illustrated in FIGS. 2B-2H, becomes available by applying know image stitches in the context of a multi-camera endoscope. To Applicant's knowledge, previously an endoscopist often had a hard time to identify the relative location of a spotted polyp relative to the location of a main forward view camera. As an example, if the endoscopist sees, on one or more computer screens, a polyp displayed to the right side of the image of the hollow channel in the center of the screen, there is a non-trivial likelihood that the polyp is actually captured by the side-view camera disposed on the left side (NOT right side, as told by the one or more computer screens) of the main shaft (relative to the forward direction of the main shaft). With the 360-degreee consolidated view of a pre-set configuration with respect to multiple pre-set cameras illustrated in FIGS. 2B-2H, the polyp captured by the left side-view camera is ALWAYS displayed to the left of the forward view image displayed in the center, thereby eliminating any aforementioned guess game by the endoscopist with respect to which side-view camera was the one that has the FOV within which the polyp is situated.

That is, in a situation where a lesion, such as a polyp, is identified during colonoscopy, it may be difficult for the endoscopist to determine which image lens is viewing the lesion. It is especially important to determine the image lens that is viewing the lesion in case a therapeutic intervention is required, in which case the lesion would need be aligned with the distal opening of the instrument channel for a therapeutic instrument to successfully target the lesion. Usually the field of view (FOV) under the forward image lens is accessible by therapeutic instruments passed through the distal opening of the instrument channel, as illustrated in FIG. 4A or FIG. 4B and said FOV designated as the "Therapeutic Zone" or "Intervention Zone".

According to one exemplary method, also shown in FIG. 4A or FIG. 4B, the FOV of each image lens is identified by a FOV marker, such as interrupted lines, on the display screen. In one implementation, the FOV marker display function is controllable by the endoscopist by means of a control switch. This enables the endoscopist to avoid superimposing FOV marker display on the images of the hollow organ, until the time when a lesion such as a polyp warranting therapeutic intervention is visualized. When a target lesion is visualized, the FOV maker display is activated and the image lens under which the lesion is visualized is determined.

Thereafter the endoscopist maneuvers the shaft of the colonoscope with forward/backward, left/right, and/or rotational motion to bring the target lesion in the 'Therapeutic Zone" or "Intervention Zone". In one implementation, the lesion may be in the FOV of at least one image lens during the maneuvering procedure, in order to make the procedure of bringing the lesion in the therapeutic zone seamless and intuitive. However, this should not be considered limiting as there may be situations when the lesion may not be in the FOV of at least one image lens during this maneuvering procedure. With the lesion in the therapeutic zone (or intervention zone), therapeutic instrument is passed through the instrument channel and directed towards the lesion and appropriate therapeutic intervention is performed.

Shadow Casting

FIGS. 5A-J are diagrams, graphs or pictorials illustrating a novel so-called "shadow casting" scheme used in connection with an advantageous configuration of a distal end of an endoscope where a set of at least two lights deployed on at least two sides of an adjacent forward view, side view, or rear view camera (disposed on, around, or otherwise adjacent to the distal end of the endoscope), according to one or more embodiments of the present disclosure.

Figure 5A:
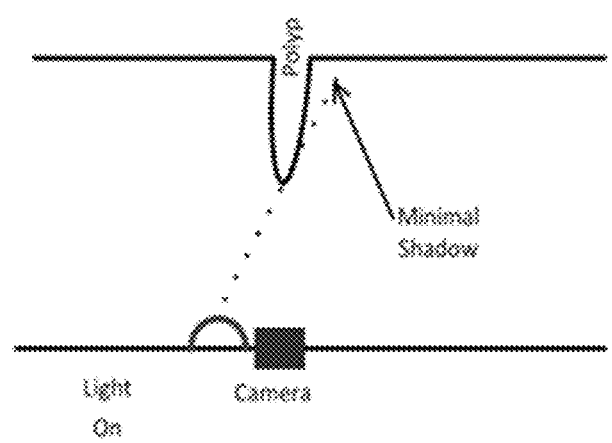
Figure 5B:
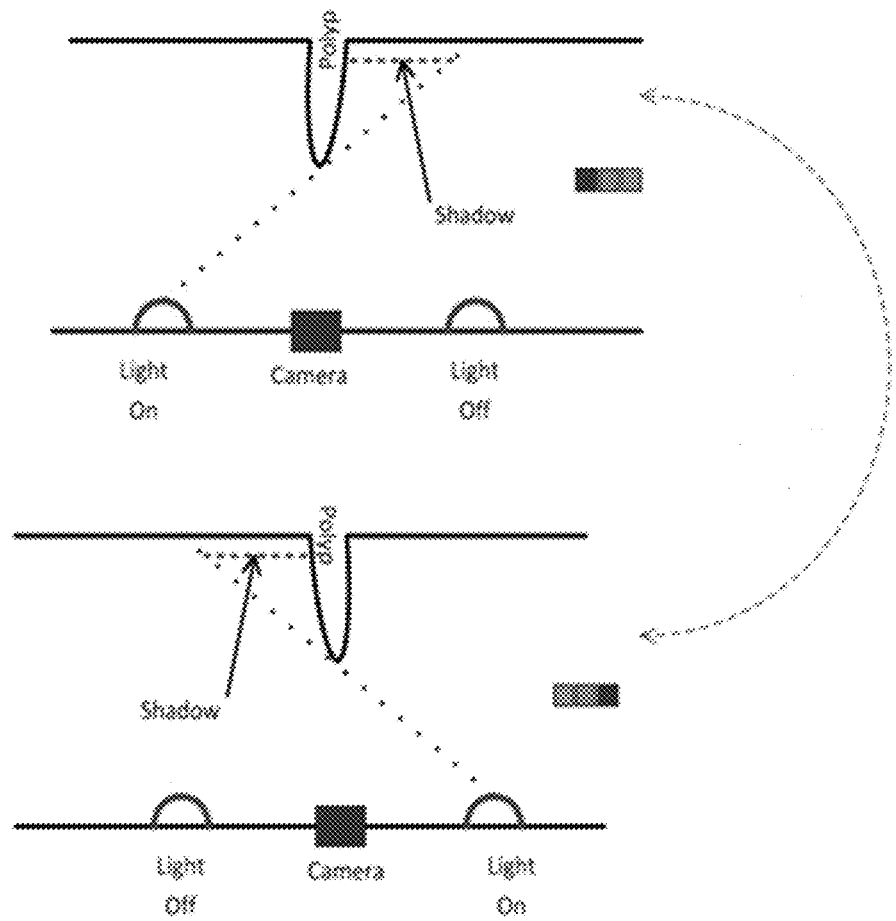
Figure 5F:
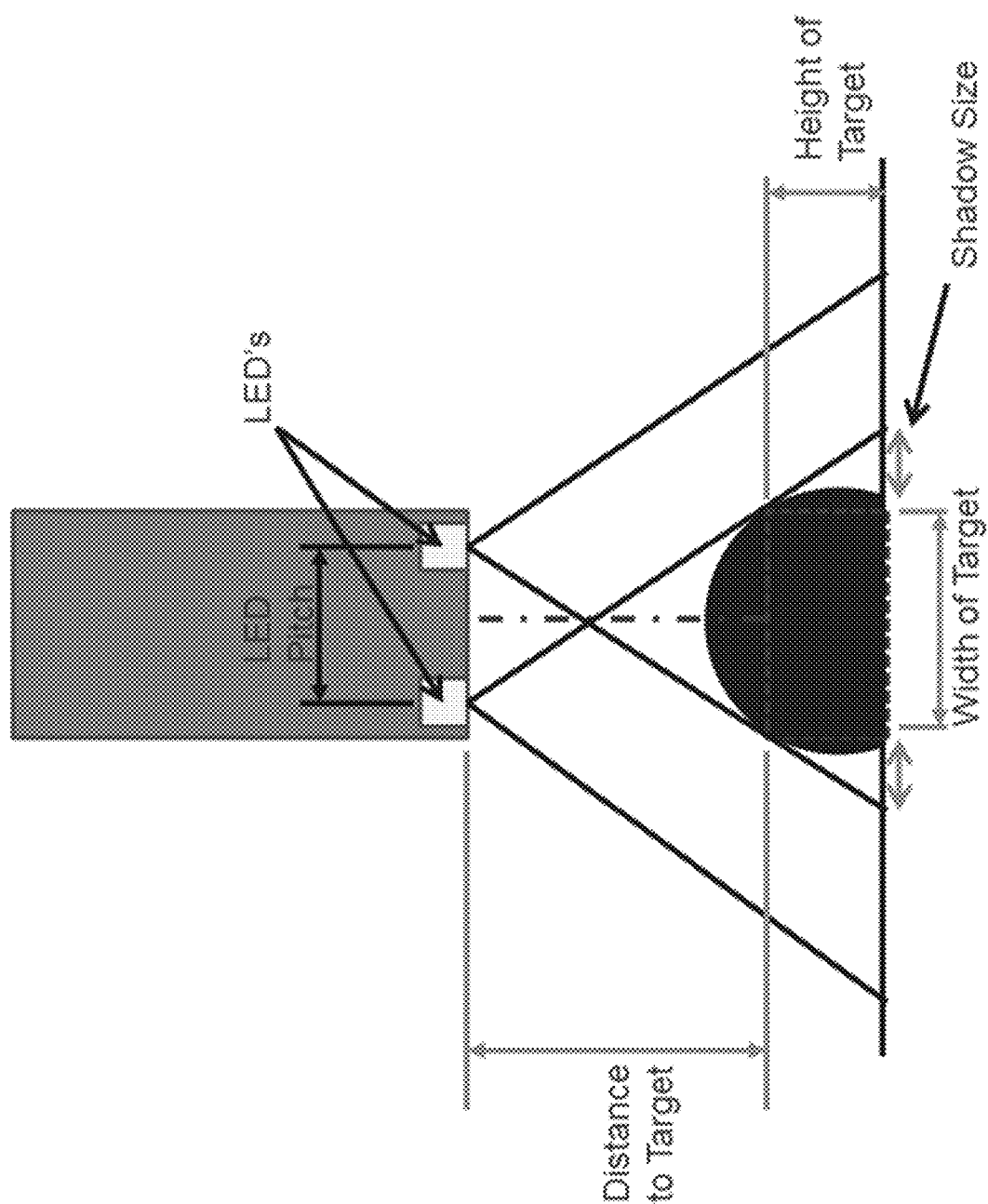
Figure 5H:
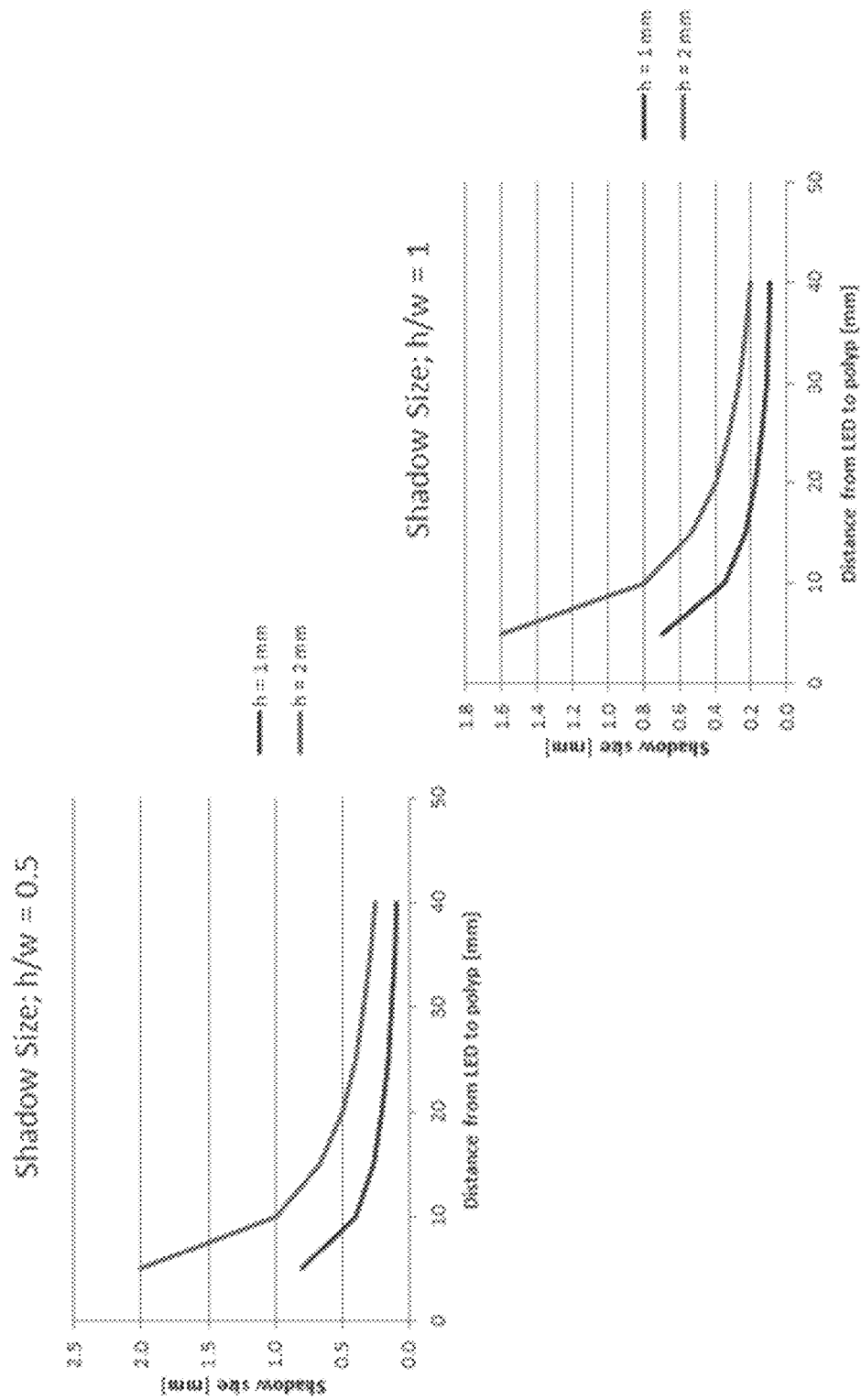
Figure 51:
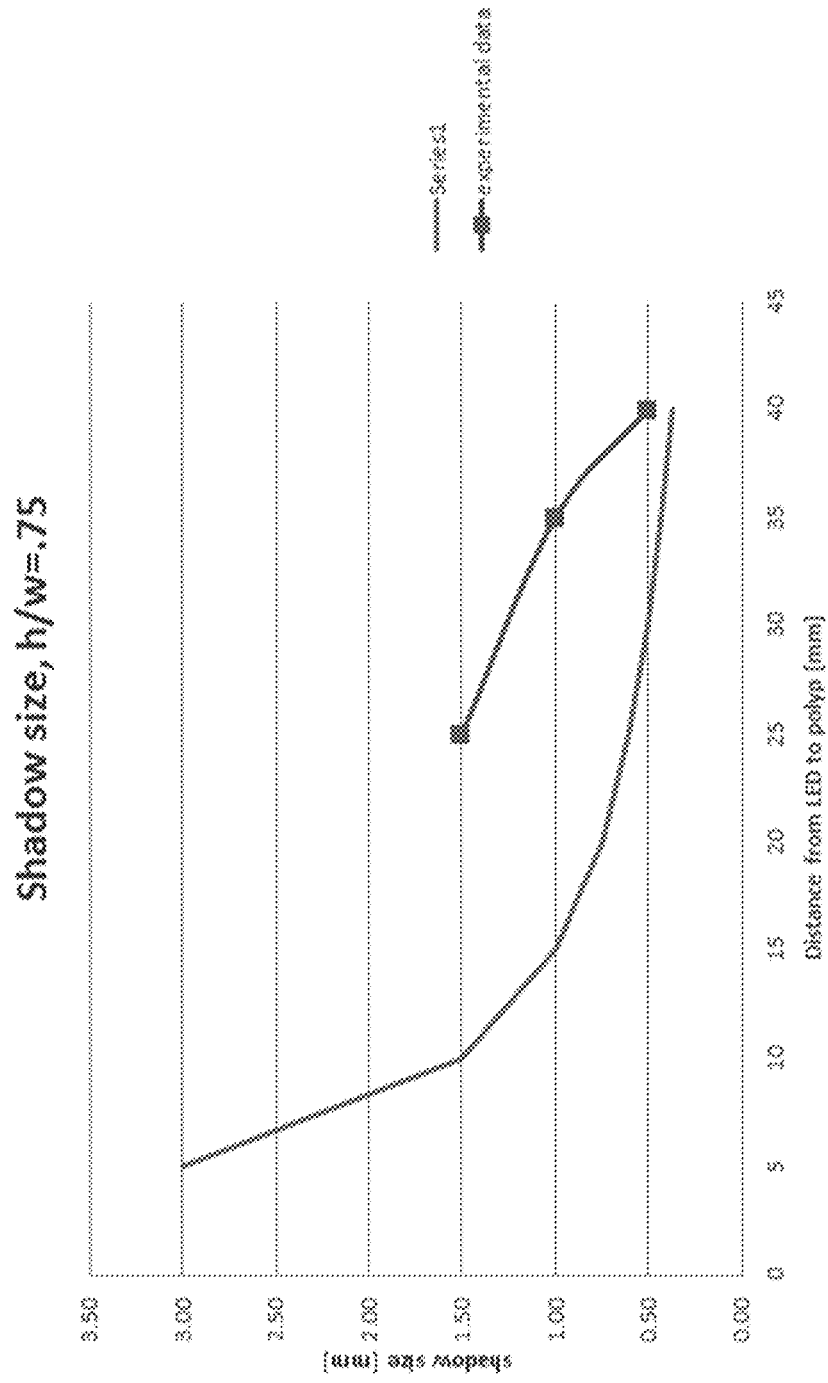

FIG. 5A illustrates a conventional way of lighting where there is typically only one light situated adjacent to a camera used to capture images within its FOV. FIG. 5B illustrates an embodiment of the disclosed novel shadow casting configuration where two lights are respectively placed on two sides of a camera and are turned on/off alternately (in connection with the use of an endoscope), thereby creating one different shadow at a time so as to get a better view of a target object, such as a polyp. FIGS. 5C-E illustrate three different configurations of shadow-casting where, in situations where differing shadows are produced and as a result, better viewing of a target object is achieved. FIGS. 5F-J illustrate the principles of using shadow casting to achieve a better viewing of a target object, such as a polyp, in connection with the use of an endoscope.

Figure 6:
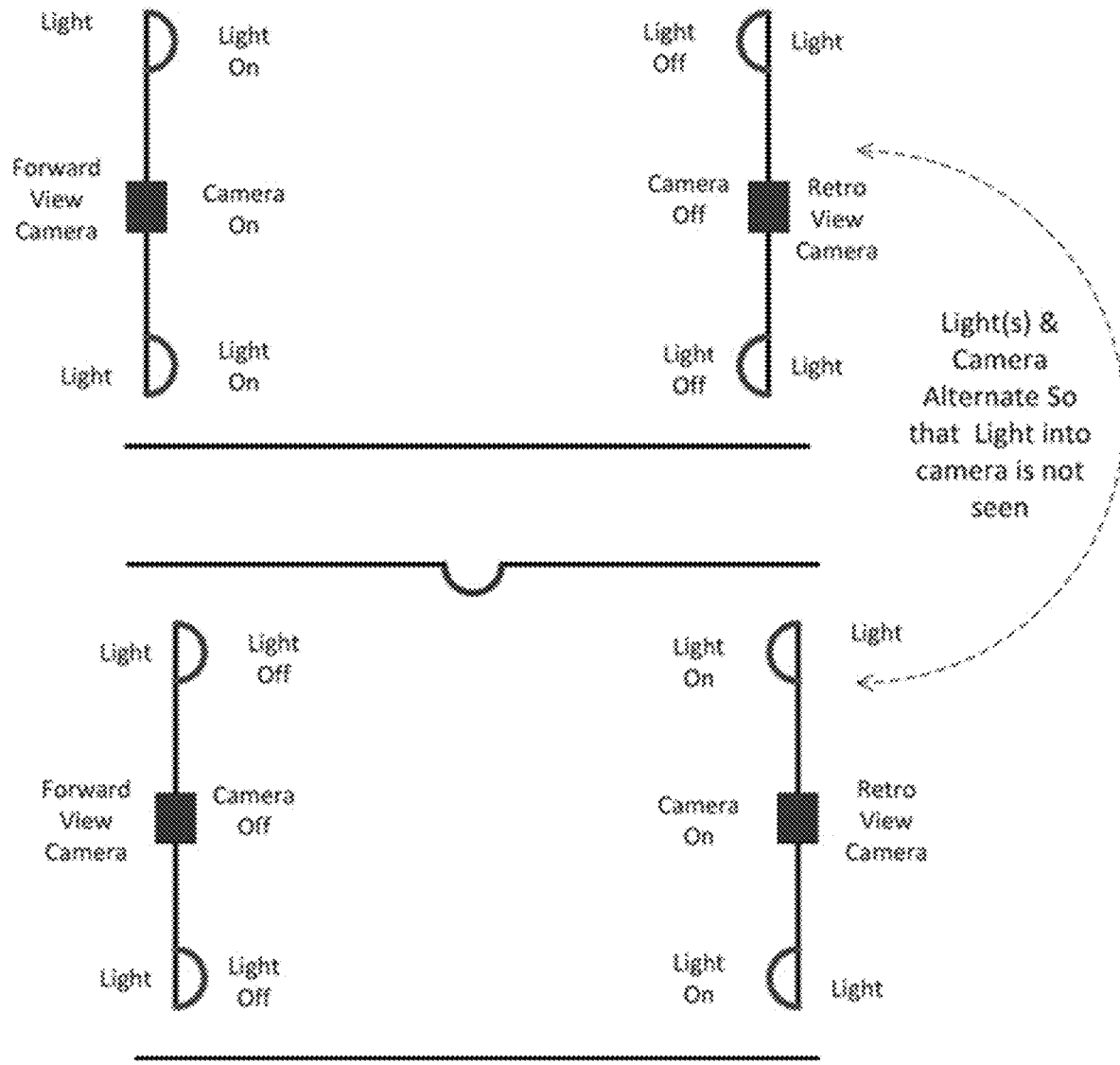
FIG. 6 is a pictorial or diagram illustrating a novel scheme relating to having "on" and "off" times of lights and cameras interleaved so as to eliminate or greatly reduce interference on one camera's image-capturing operation by lights for another camera (which greatly facilitates the discovery of a lesion or polyp with images captured by a camera), as used in connection with an advantageous configuration of a distal end of an endoscope where a set of at least two lights deployed on at least two sides of an adjacent forward view, side view, or rear view camera disposed on, around, or otherwise adjacent to the distal end of the endoscope, according to one or more embodiments of the present disclosure.

FIG. 6 illustrates a novel scheme relating to having "on" and "off" times of lights and cameras interleaved to prevent or reduce interference or intervention of image-capturing of one camera by a light for another camera, and vice versa, so as to facilitate the discovery of a lesion or polyp, as used in connection with an advantageous configuration of a distal end of an endoscope where a set of at least two lights deployed on at least two sides of an adjacent forward view, side view, or rear view camera disposed on, around, or otherwise adjacent to the distal end of the endoscope, according to one or more embodiments of the present disclosure.

L' shaped Rear View Catheter

FIGS. 7A-G illustrate exemplary configurations and implementations of a novel L-shaped rear view (retro-view) catheter (hereinafter simply referred to as L-catheter) used in connection with an endoscope (particularly, a main instrument channel or a dedicated channel of an endoscope) for providing a retrograde view adjacent to a distal end of the endoscope when deployed adjacent thereto, according to one or more embodiments of the present disclosure.

Specifically, as illustrated in FIGS. 7A-G, the long limb of the 'L' rear view catheter (also simply referred to as an "L-catheter") is of thickness with a diameter that is smaller than the diameter of the hollow channel of the endoscope. The endoscope facing side of the short limb of the 'L' rear view catheter houses one or more image lenses such as CCD or CMOS, as illustrated in 7G. The endoscope facing side of the short limb of the 'L' rear view catheter also houses one or more lights, such as a LED bulb, as illustrated in 7G.

Figure 7A:
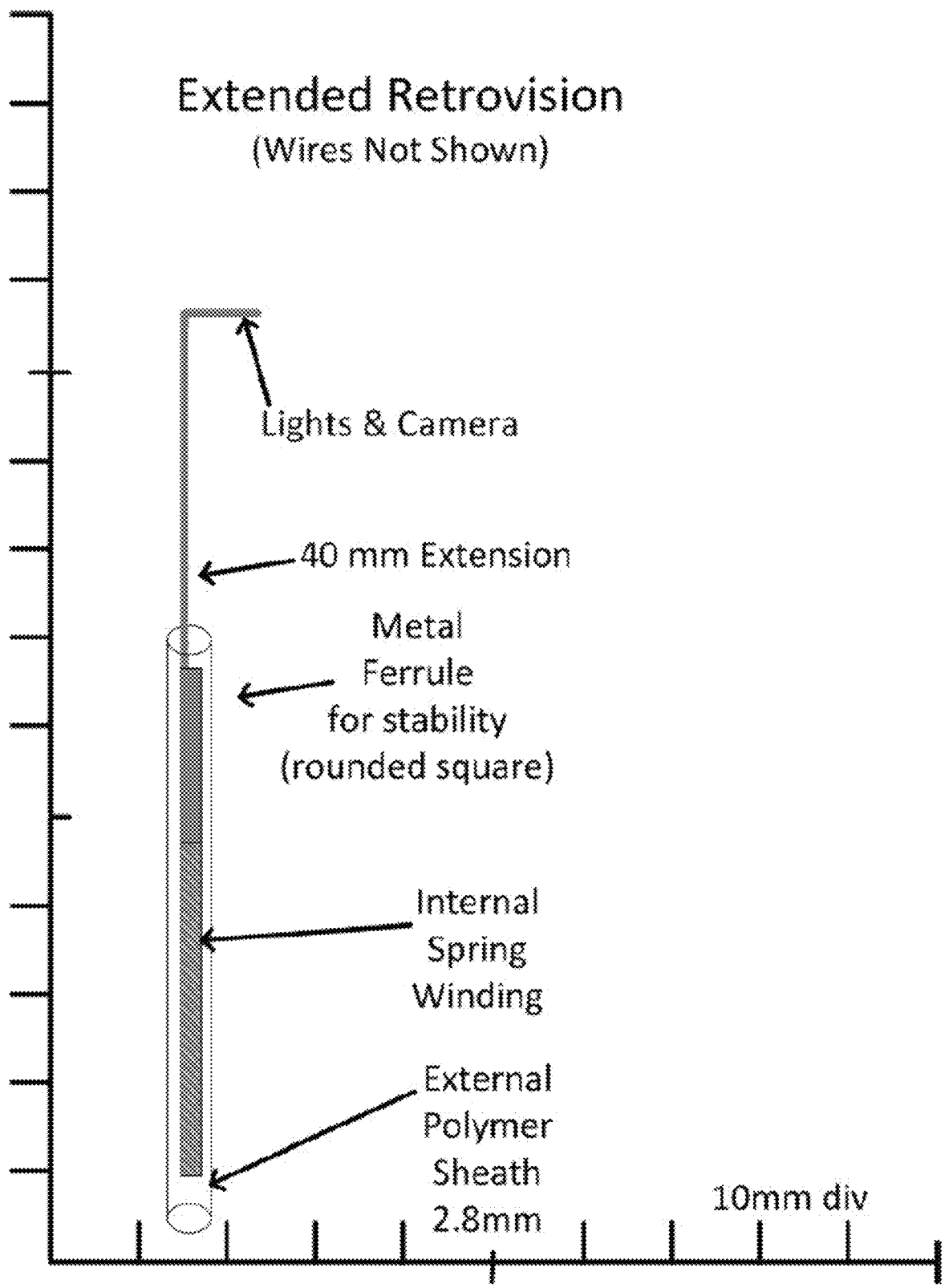
Figure 7B:
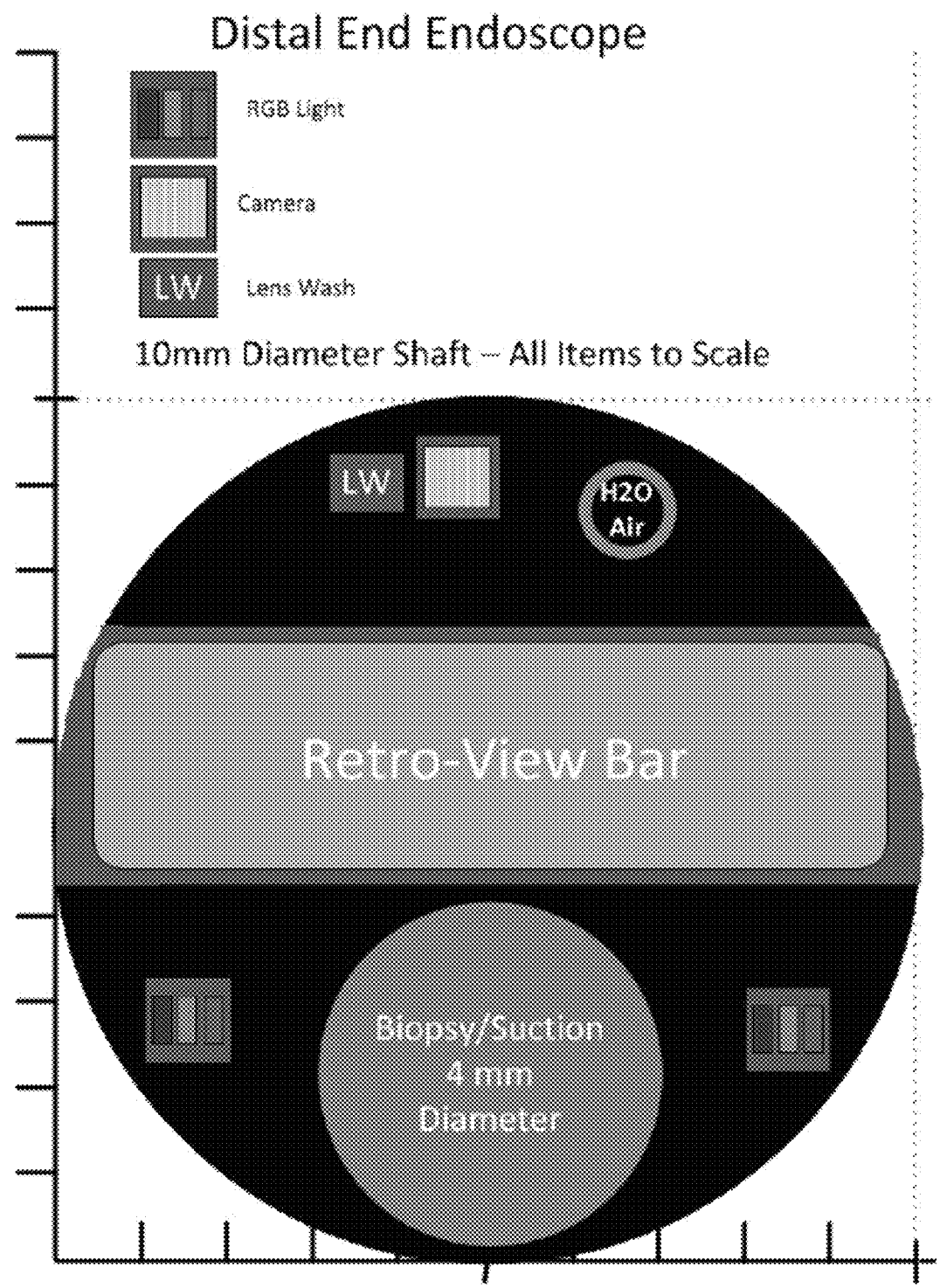
Figure 7C:
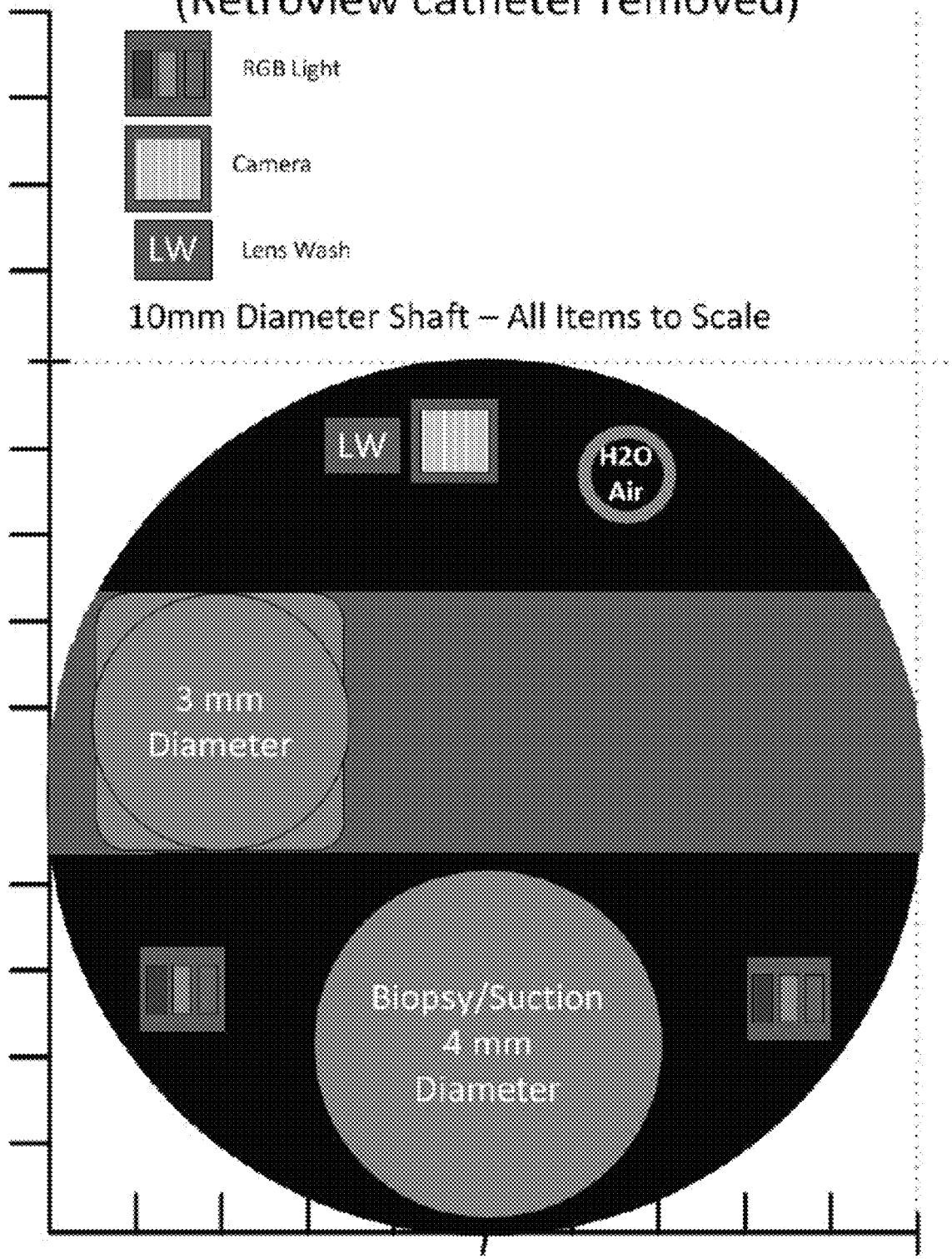
Figure 7G:
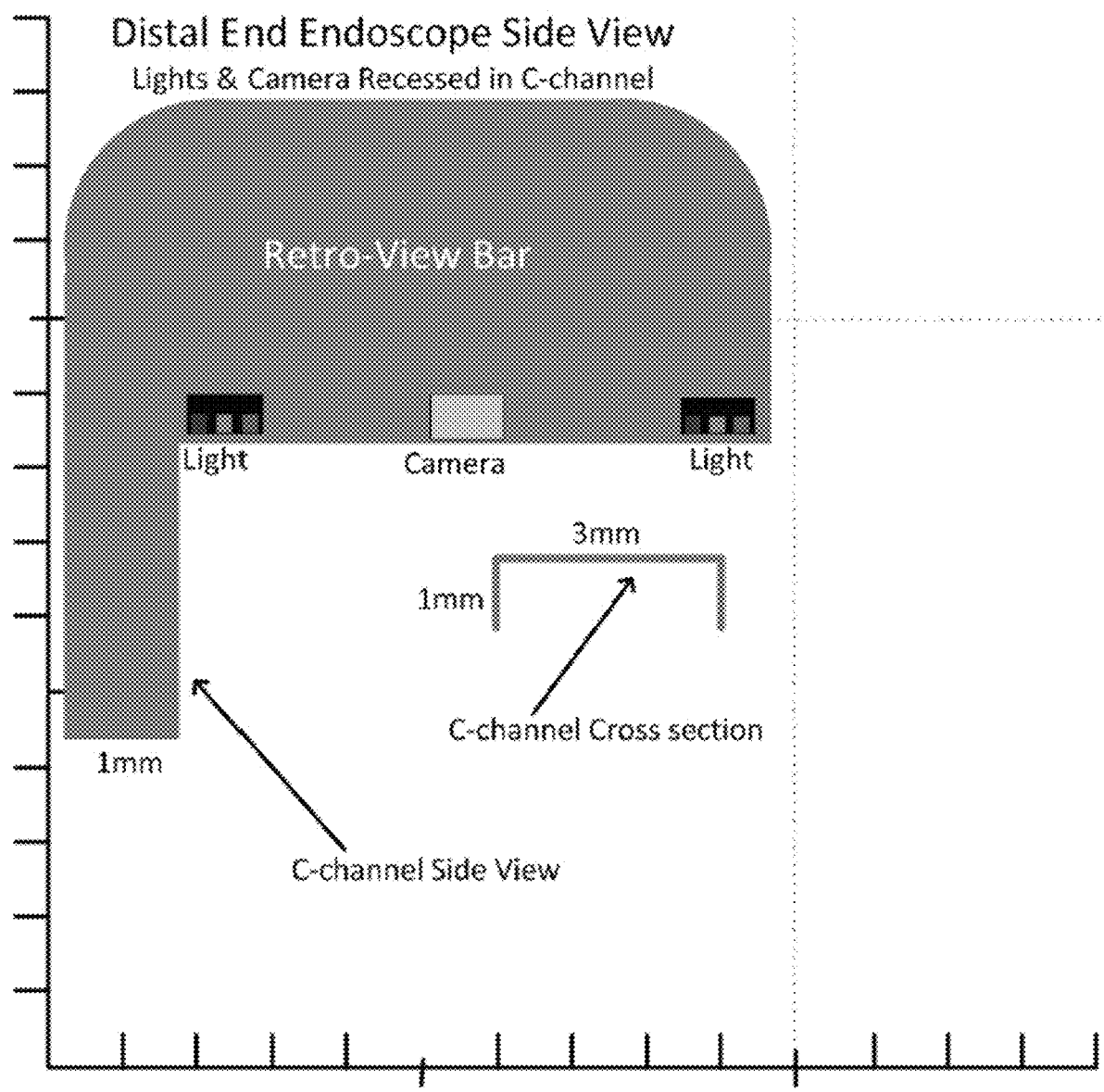
Figure 8A:
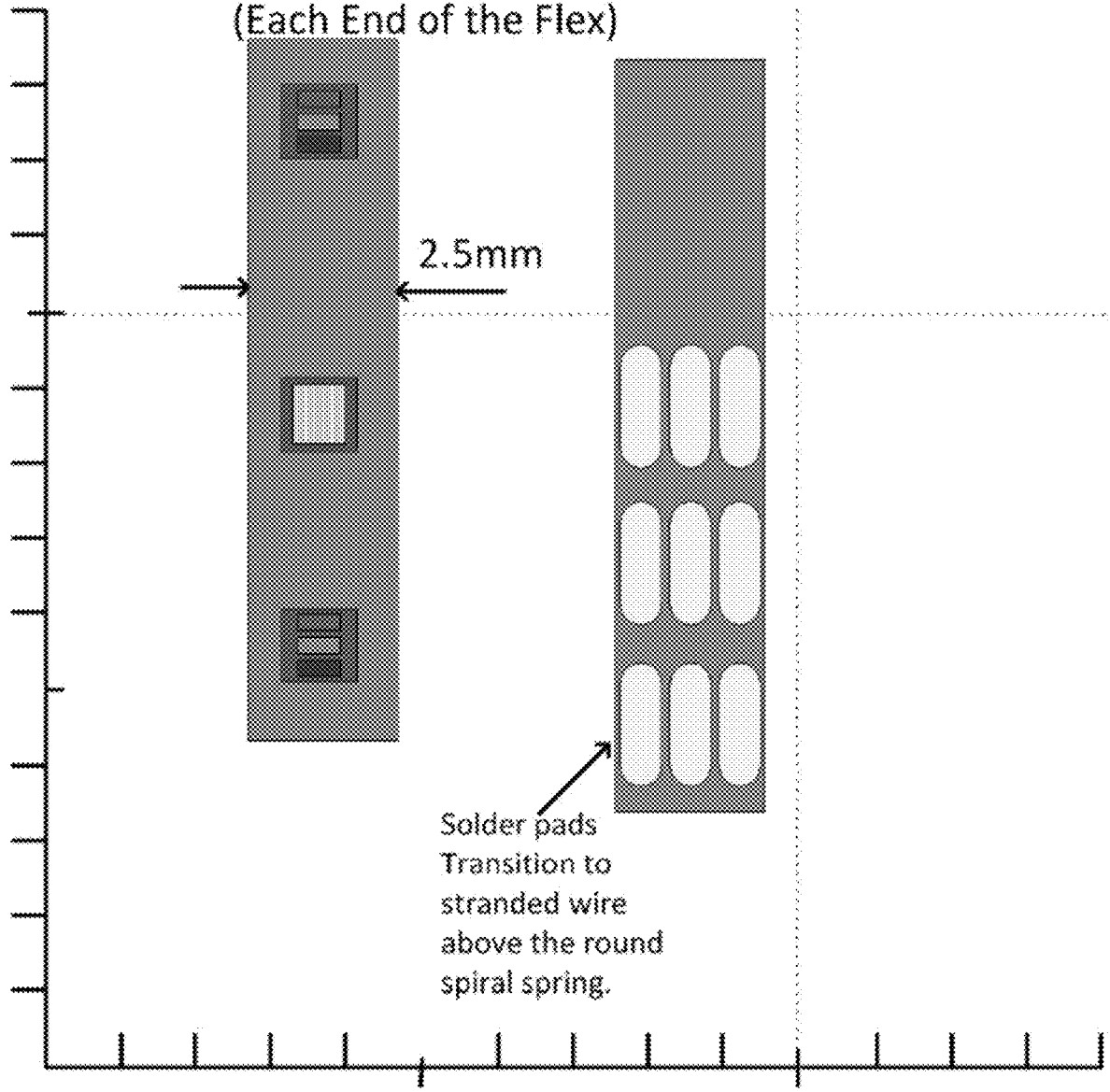
Figure 8B:
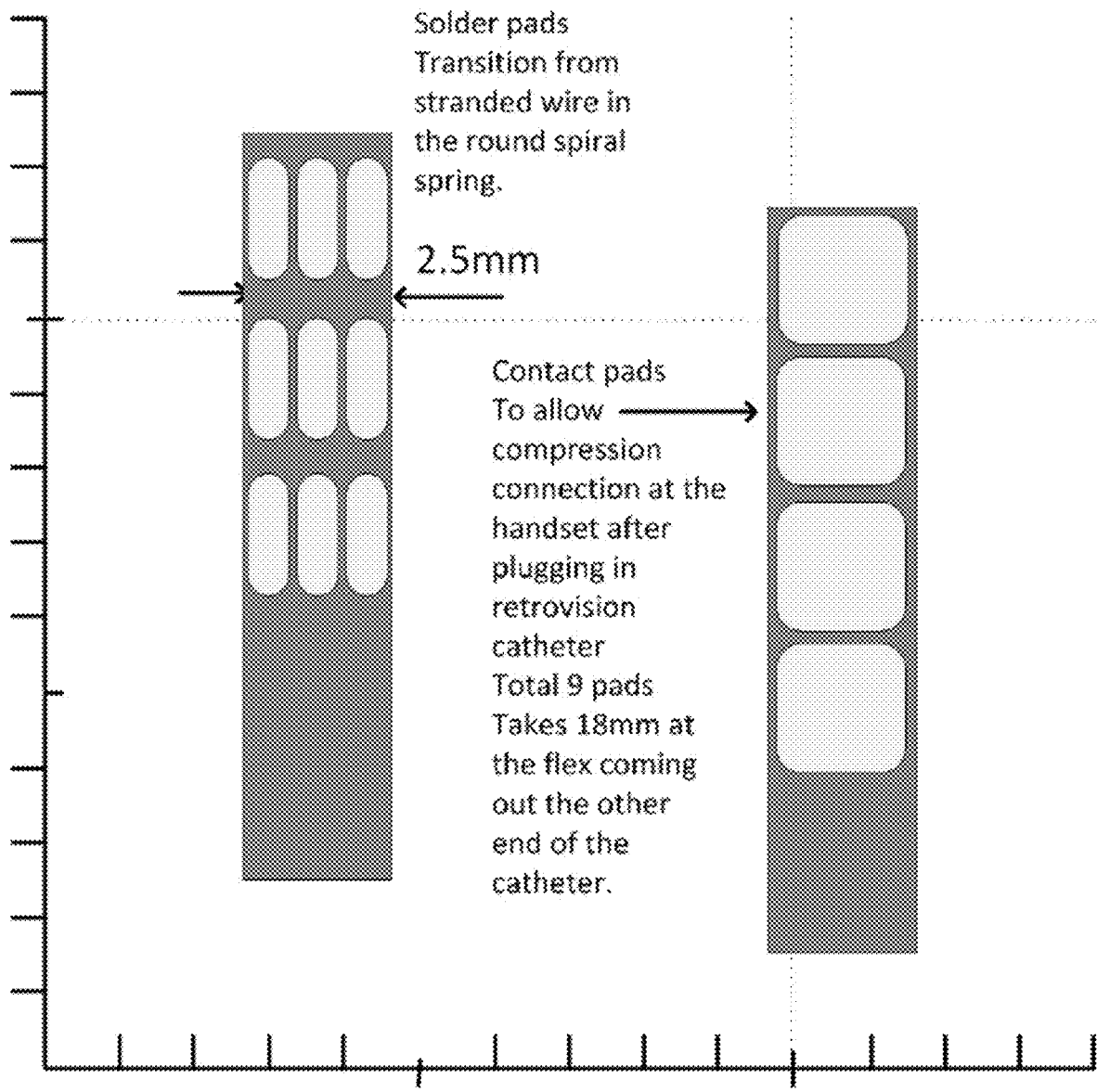
Figure 8C:
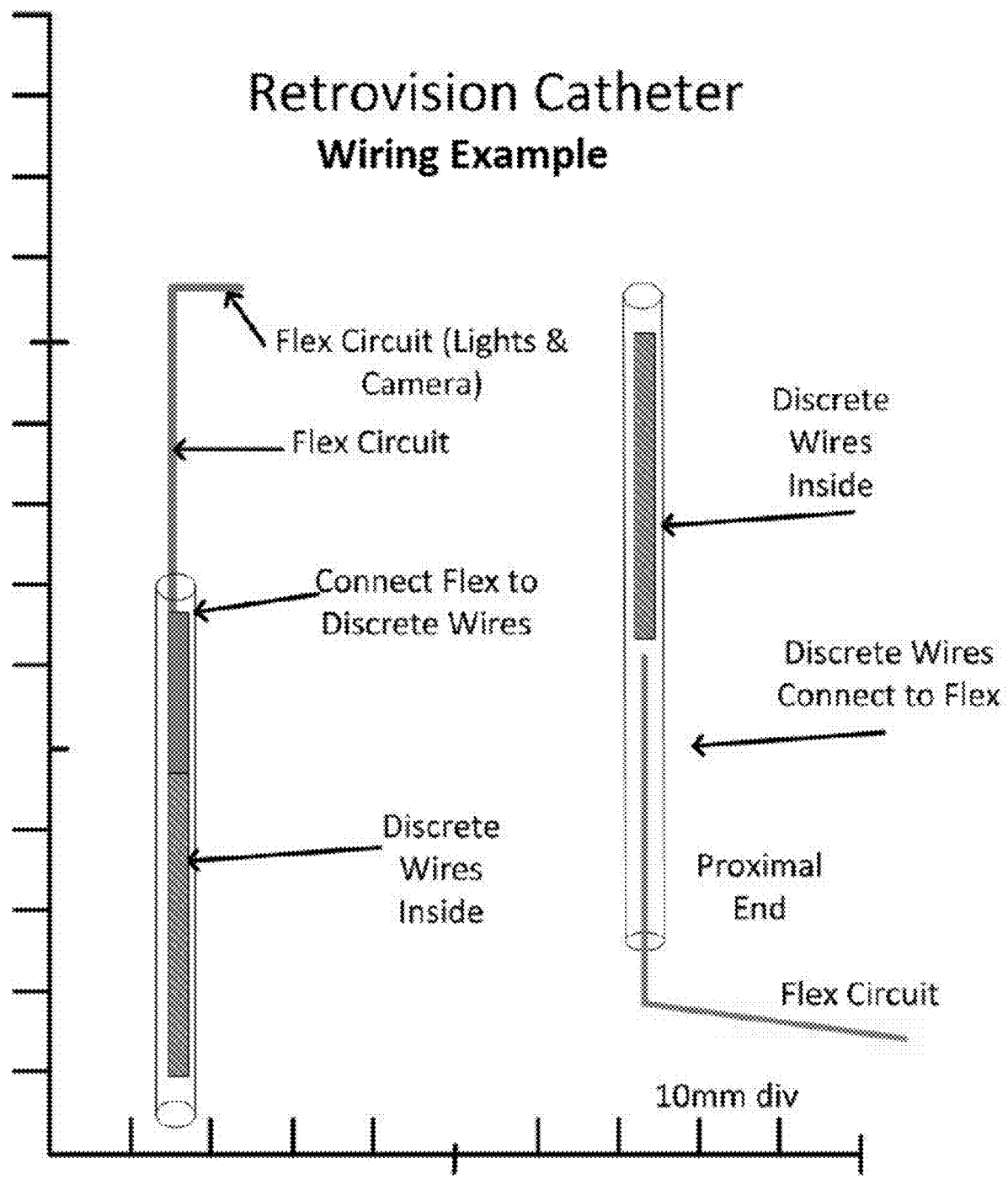
Figure 8D:
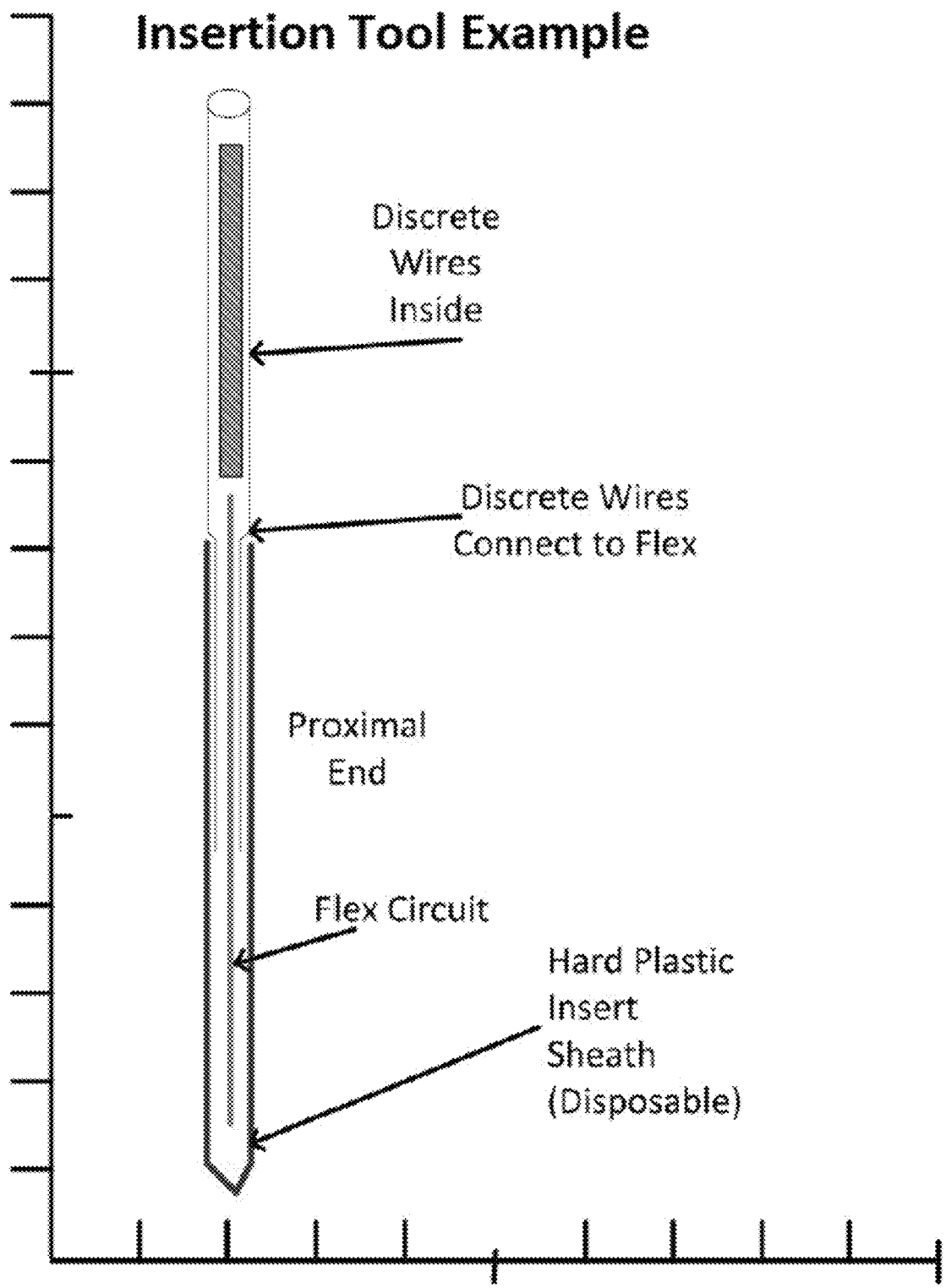

The image lenses and the light is connected to image processor, power source and light source when light guide is used as a light source, e.g., via electric cables running through the long limb of the rear view catheter. In one implementation, the short and the long limb of the 'L' rear view catheter is connected by a flexible link, which may be made out from a shape memory material, so as to enable the 'L' rear view catheter to traverse sharp turns of the colon and thereafter automatically resume the rear facing configuration with respect to the distal end of the endoscope, as illustrated in FIG. 7B. It also enables the 'L' rear view catheter to be inserted antegrade into the hollow channel of the endoscope till the short limb of the rear view catheter urges distal to the distal end of the endoscope, whereafter it assumes a rear facing configuration with respect to the distal end of the endoscope.

In one embodiment, the proximal end of the hollow channel of the endoscope has electrical connector pins that are operatively connected to a power source, image processor and light source (when light guide is used). The proximal end of the long limb also has reciprocal electrical connector pins that, when reciprocally positioned, operatively engages with the electrical connector pins in the hollow channel of the endoscope. When the electrical connector pin sets are engaged, the image lens and the light source of the 'L' rear view catheter is automatically connected to power source, image processor and light source (when used), without requiring any external connections. This feature of the device makes the device user friendly.

In one embodiment of this endoscope system, there is, e.g., a retaining mechanism, such as a groove, at the distal end of the endoscope that reciprocally accommodates the short limb of the 'L' rear view catheter when the 'L' rear view catheter is engaged inside the hollow channel of the endoscope. In one embodiment, the endoscope has a dedicated hollow channel for the rear view catheter, in addition to a separate instrument channel. The advantage of a dedicated rear catheter hollow channel is that is enables the use of a separate instrument channel for performing therapeutic interventions while the rear view catheter continues to be engaged with the endoscope and ready to provide a rear view, without requiring repeated insertions and withdrawals intra operatively.

FIGS. 8A-E illustrate exemplary configurations and implementations of the novel L-catheter in connection with flex circuit and wiring as related to cameras and lights deployed on the short limb of the L-catheter, according to one or more embodiments of the present disclosure.

Figure 12A:
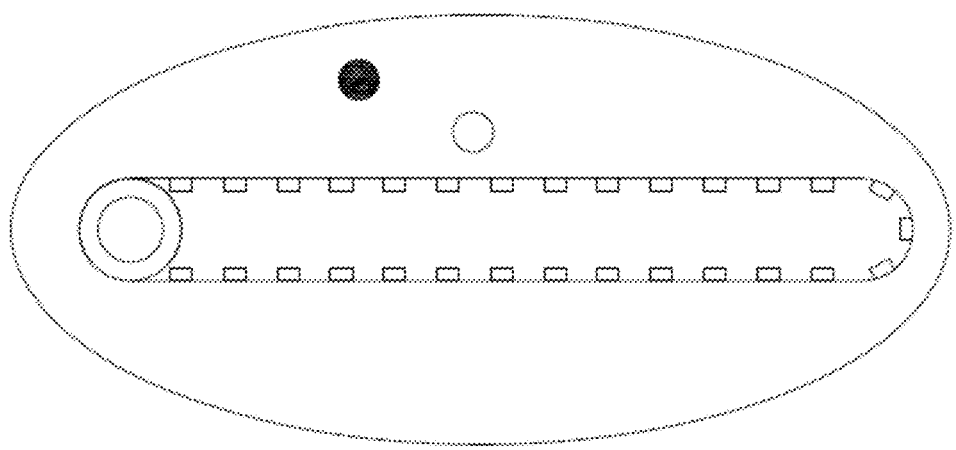
FIGS. 12A-C are cross section views with respect to the front of a contraception (device) disposed on the distal end of a main shaft of the endoscope, illustrating an exemplary configuration of a housing within the distal end contraption (device) adapted to receive and securely rest the short limb (retro-view bar) in a resting mode where the L-catheter is not being actively deployed or otherwise positioned to capture an intended rear view, according to one or more embodiments of the present disclosure.
Figure 12B:
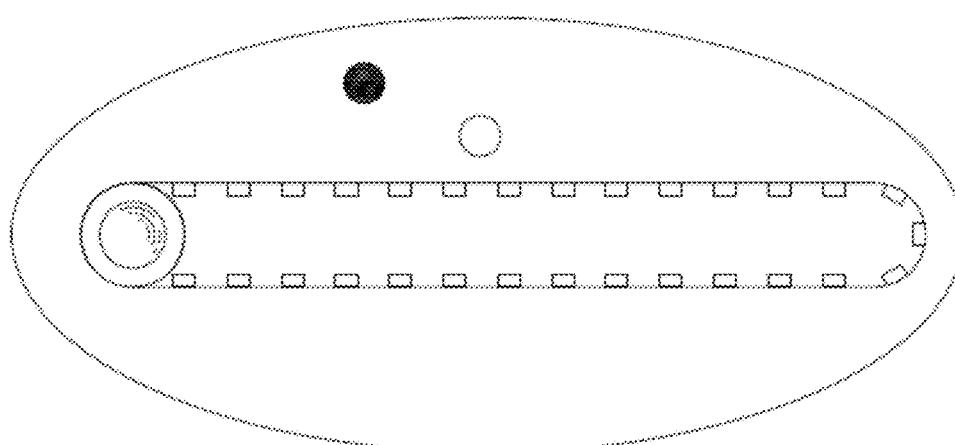
Figure 12C:
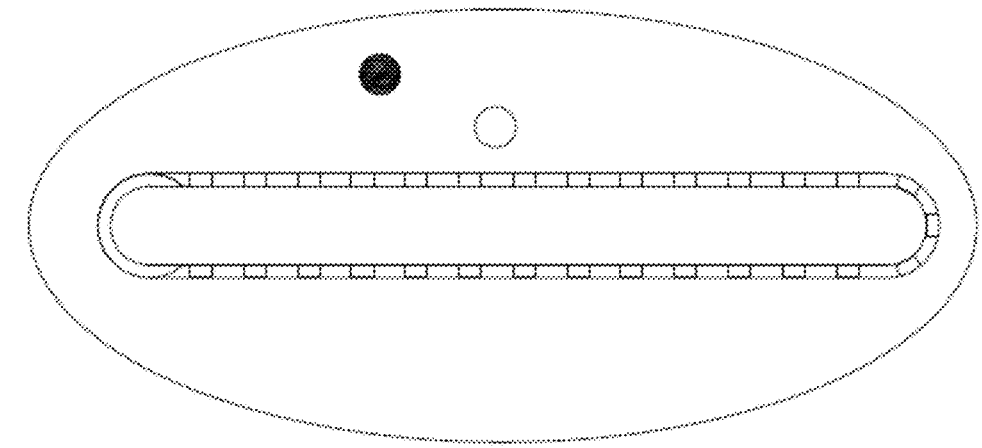

FIGS. 12A-C illustrates an exemplary configuration of a housing (for retaining the short limb) within the distal end contraption (device) for receiving and securely resting the short limb (retro-view bar) in a resting mode where the L-catheter is not being actively deployed (e.g., extended beyond distal end 100) or otherwise positioned to capture a rear view, according to one or more embodiments of the present disclosure. Specifically, the long limb of the 'L' rear view catheter may be back fed (retrograde) into the hollow channel of the endoscope till the proximal end of the long limb of the catheter is inserted to a predetermined position inside the hollow channel. In this position, the short limb of the 'L' rear view catheter rests reciprocally in the groove (or other similar retaining mechanism) on the distal end of the endoscope, as illustrated in FIG. 12C.

When the surgeon wishes to obtain a rear view of the hollow organ, the 'L' rear view catheter is advanced in the hollow channel of the endoscope extending the short limb of the 'L' rear view catheter distal to the distal end of the endoscope, as illustrated in FIG. 7E. In this position, the short limb of the 'L' rear view catheter extends out from the distal end of the endoscope to an extent where it is positioned to provide a rear view of the hollow organ relative to the distal end of the endoscope. Additionally, in this position the electrical connections on the proximal end of the 'L' rear view catheter comes in contact with the electrical connection of the hollow channel of the endoscope, as illustrated in FIGS. 15B and 15C.

Figure 15A:
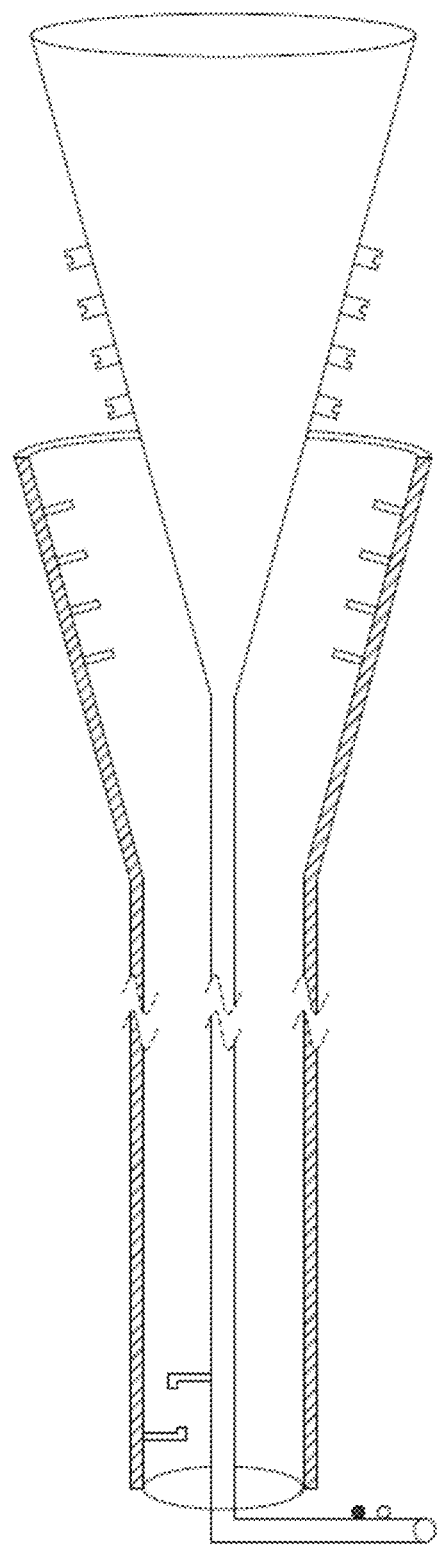
FIGS. 15A-C are perspective views with respect to an outer channel (such as an instrument channel or a dedicated channel for a rear view catheter) within a hollow channel of a main shaft of an endoscope, illustrating exemplary novel "male/female connectors" and "stop-measure" configurations for deploying a rear view catheter so that the catheter may be conveniently deployed to switch from an inactive mode to an active mode with respect to connecting rear view cameras and light sources to the main processor box of the parent endoscope upon the rear view catheter reaching an active position suitable for capturing an intended rear view, according to one or more embodiments of the present disclosure.
Figure 15B:
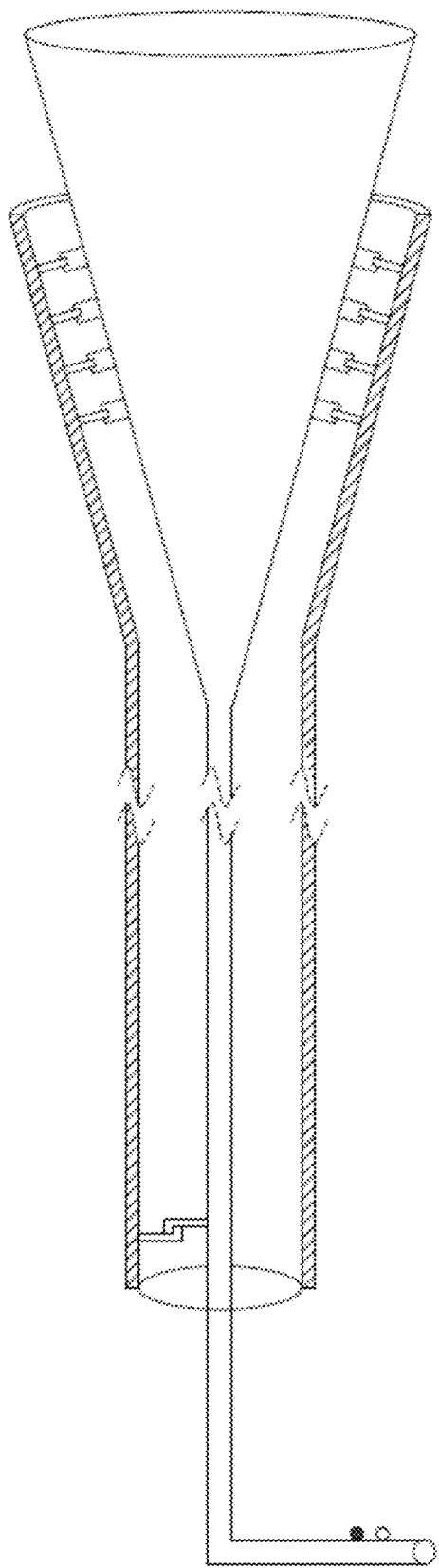
Figure 15C:
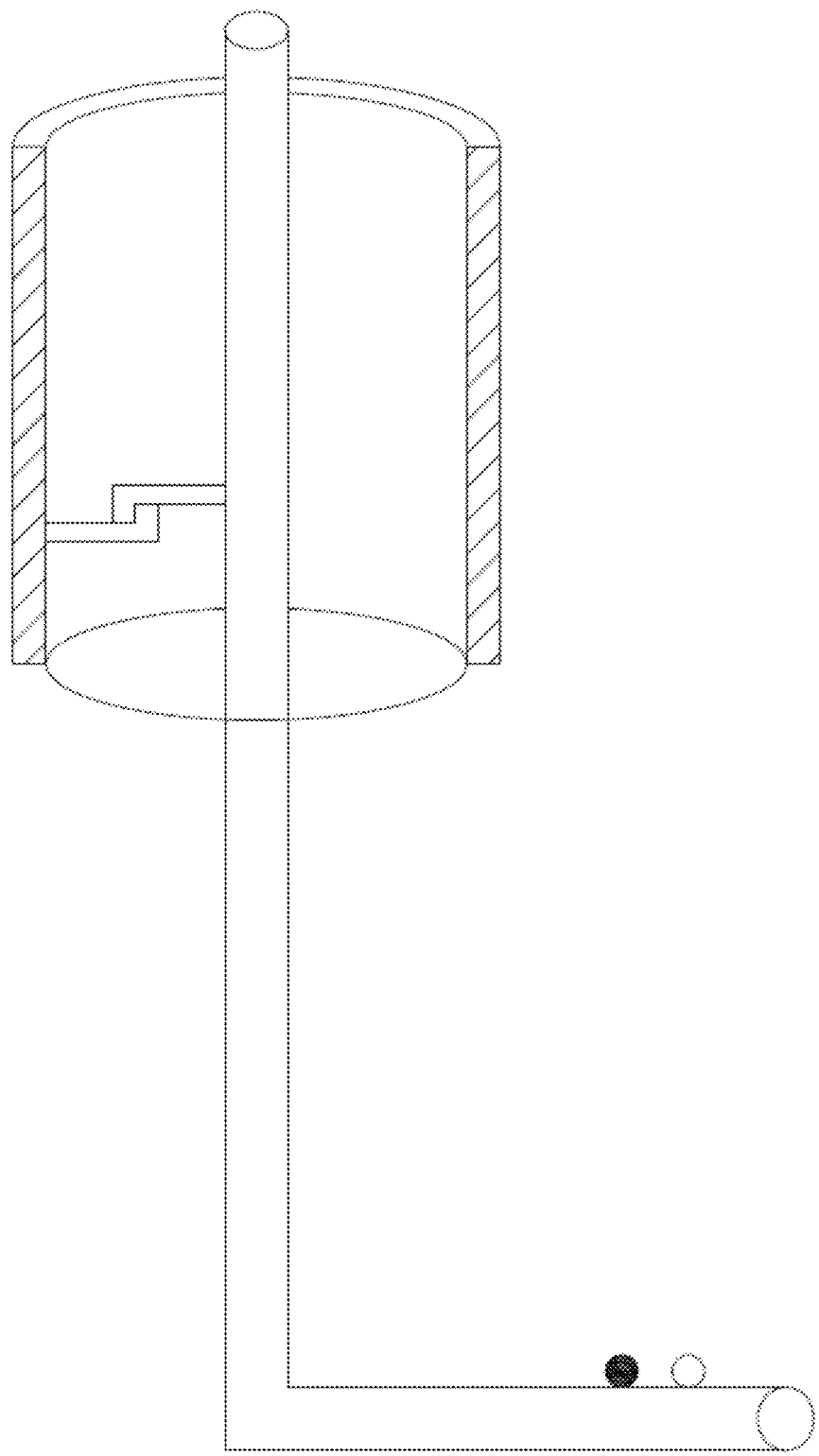

According to another exemplary method of use, the 'L' rear view catheter is fed antegrade into the hollow channel of the endoscope till the short limb of the 'L' rear view catheter extends out from the distal end of the endoscope to an extent where it is positioned to provide a rear view of the hollow organ relative to the distal end of the endoscope, as illustrated in FIGS. 15B-C. Additionally, in this position, the electrical connections on the proximal end of the 'L' rear view catheter come in contact with the electrical connection of the hollow channel of the endoscope, as illustrated in FIGS. 15B-C. When not in use, the proximal end of the long limb of the catheter is retracted to a predetermined position inside the hollow channel, as illustrated in FIG. 12C. In this position, in one embodiment, the short limb of the 'L' rear view catheter rests reciprocally in a groove on the distal end of the endoscope, as illustrated in FIGS. 12A-C and FIG. 15A. Thereafter, when the surgeon wishes to obtain a rear view of the hollow organ, the 'L' rear view catheter is advanced distally in the hollow channel of the endoscope extending the short limb of the 'L' rear view catheter distal to the distal end of the endoscope, as illustrated in FIGS. 15B, 15C and 7E. As discussed above, in this position, the short limb of the 'L' rear view catheter extends out from the distal end of the endoscope to an extent where it is positioned to provide a rear view of the hollow organ relative to the distal end of the endoscope.

Air/Water Channel

Figure 10A:
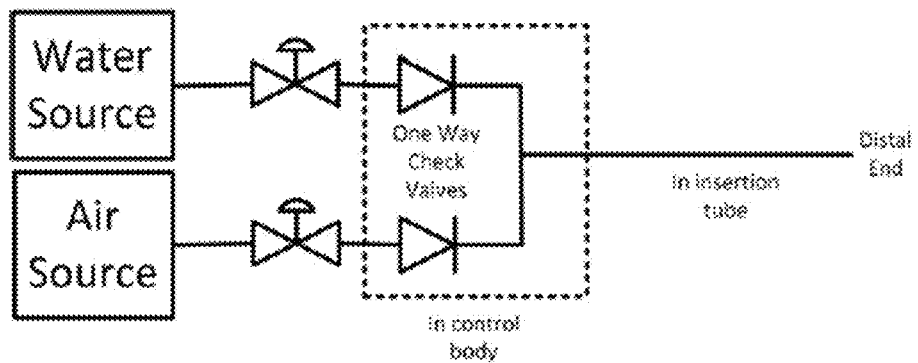
FIGS. 10A-C are diagrams or perspective views illustrating exemplary novel configurations of main and periphery (side) air/water channels provided in connection with an endoscope having multiple cameras each having a different FOV, according to one or more embodiments of the present disclosure.
Figure 10B:
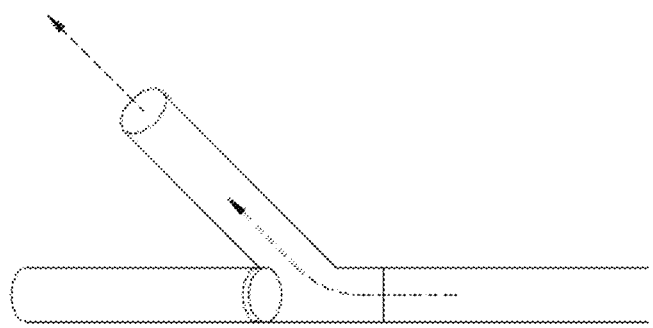
Figure 10C:
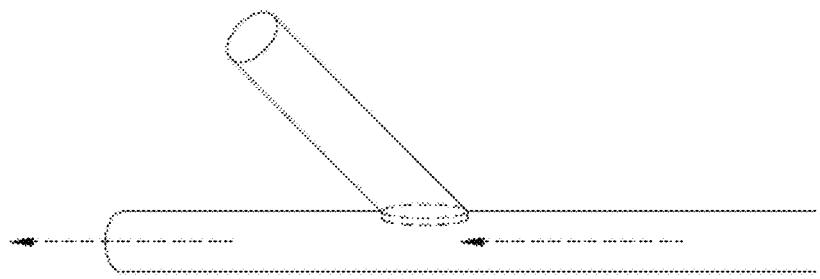

FIGS. 10A-C are diagrams or perspective views illustrating exemplary novel configurations of main and periphery (side) air/water channels in connection with an endoscope having multiple cameras each having a different FOV, according to one or more embodiments of the present disclosure.

As mentioned, the endoscope system of the present disclosure has an air/water channel servicing one or more image lens and/lights (when more than one image lens and/or lights is present). As disclosed herein, each fixed image lens and/or light of the endoscope is serviced by an air/water channel, positioned such that when air/water is pushed out of the air/water channel outlet, it is directed towards the corresponding image lens and/or light source. Referring to FIGS. 10B and 10C, in one embodiment, the air/water channels servicing the image lens and/or light source branches off from the main air/water channel with a control valve (which, as illustrated, can either let the air/water only flow through the side air/water channel (branched off from the main air/water channel) or let the air/water only flow through the main air/water channel).

With regard to main and side air/water channels, one or more of the following may be provided: i) sum of diameter of all side air/water channel is substantially equal to the diameter of the main air/water channel; and/or ii) the side air/water channels are substantially of the same diameter. These functions may be beneficial in adequate washing of the corresponding image lens and/or light source. However, the diameter of the side air/water channel may also be customized based on the needs of the corresponding image lens and/or light source. In case a particular side image lens and/or light source needs more washing than other image lens/light source, then the diameter of the corresponding air/water channel can be made larger. Alternatively or additionally, as illustrated in FIGS. 10B and 10C, a control valve can also be used to distribute the volume of water/air form the main air/water channel to different air/water channels. According to another embodiment, each image lens and/or light source on the endoscope is serviced by a dedicated air/water channel.

No Light Source

It is also disclosed that when a rear view catheter or a front rear view module (one example of which is described in U.S. Pat. No. 6,736,773, titled "Endoscopic Vision System", whose entire disclosure is also hereby incorporated by reference), is used in conjunction with an endoscope with multiple side rear view modules (having one or more side view light and so on), the rear view catheter or the front rear view module may not need its own light as the field of view under the rear view catheter or the front rear view module is adequately illuminated by the side light of the side rear view modules. In this situation, a rear view catheter or a front rear view module can be made thinner, as the need to have a light source and corresponding cables is obviated. Additionally, in this situation, there is less interference between the first image lens and the rear view catheter/front rear view module. In the above examples of embodiments of the endoscope, a parent endoscope can have any number of image lenses OR lights and that should not be considered limiting.

As related to the above-mentioned use of LEDs (which may result in no need for light source for some cameras disposed adjacent to distal end 100 of an endoscope), FIG. 11 is a pictorial illustrating exemplary LEDs relating to a disclosed novel use of LEDs to provide lighting for one or more cameras used in connection with, e.g., a rear view catheter (such as an L-catheter) deployed adjacent to a distal end of an endoscope or an endoscope having multiple simultaneous views, according to one or more embodiments of the present disclosure.

Trailing Suction Catheter

Specifically, it is a common practice in the field of Endoscopy to insufflate air into a hollow organ to dilate the hollow organ to enable adequate visualization. Insufflated air sometime causes discomfort to the patient. Hence it is usual to suction as much air as possible during withdrawal of the endoscope. In the endoscope embodiments of the present disclosure, it is possible that more air may need to be insufflated into the hollow organ to enable adequate and optimal visualization by the multiple image lenses disposed on the parent endoscope. This could potentially cause discomfort in some patients.

Figure 13:
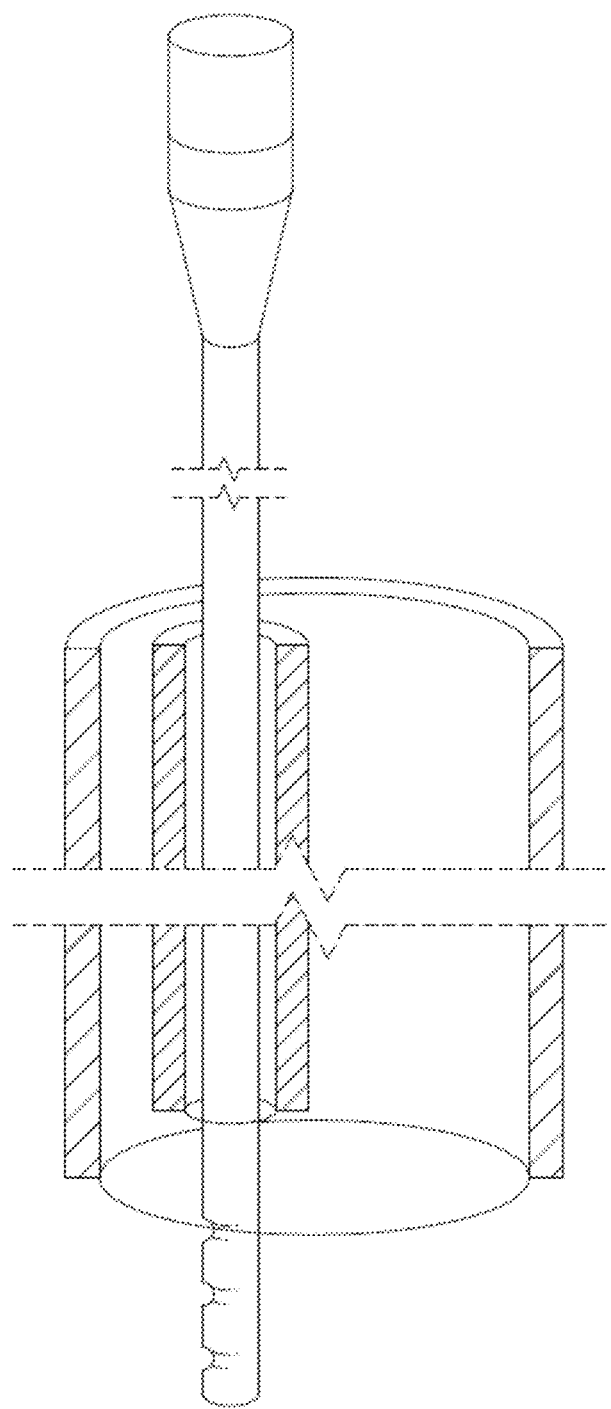
FIG. 13 is a perspective view illustrating a novel "trailing suction catheter" scheme in connection with, e.g., a rear view catheter (such as an L-catheter) deployed adjacent to a distal end of an endoscope or an endoscope having multiple simultaneous views, according to one or more embodiments of the present disclosure.

FIG. 13 illustrates a novel "trailing suction catheter" scheme in connection with, e.g., a rear view catheter (such as an L-catheter) deployed adjacent to a distal end of an endoscope or an endoscope having multiple simultaneous views, according to one or more embodiments of the present disclosure. Referring to FIG. 13, a rear view catheter has an extendable "suction catheter" that extends out distally from the rear view catheter, when the rear view catheter is deployed by extending it from the rear view channel from the endoscope. The exemplary suction catheter comprises a thin tubular structure comprising of distal, mid and proximal sections, and has one or more holes, as illustrated, in the distal section. It is operatively connected to a suction pump, as illustrated, on the proximal end. Once the rear view catheter is deployed for rear viewing of a hollow organ—which typically takes place when the parent endoscope is withdrawn from the hollow organ—the suction catheter is extended distally from the rear view catheter and the suction pump is turned on. As the parent endoscope is withdrawn, the suction catheter trails behind the parent endoscope (and the rear view catheter) and suctions out the air from the distal portion of the hollow organ which has already been visualized by the parent endoscope (and the rear view catheter).

Alternatively, the suction catheter can be decoupled from a rear view catheter such that it is independently operable regardless of the whether a rear view catheter is used or not. In this situation, a suction catheter is passed independently through a hollow channel of the parent endoscope and extended distally from the distal end of the parent endoscope such that it trails behind the parent endoscope when the parent endoscope is withdrawn from the hollow organ. In this position, when operatively connected to a suction pump, the rear view catheter suctions air from an area of the hollow organ that has already been visualized by the parent endoscope.

Novel Proximal Connections of a Rear View Catheter

FIGS. 15A-C illustrate exemplary novel "male/female connectors" and "stop-measure" configurations for deploying a rear view catheter so that the catheter can be conveniently deployed to switch from an inactive mode to an active mode with respect to connecting rear view cameras and light sources to the main processor box of the endoscope upon the rear view catheter reaching an active position suitable for capturing a rear view, according to one or more embodiments of the present disclosure.

Referring to FIGS. 15A-C, in one example, a rear view catheter reversibly engages and disengages with a rear view channel of the parent endoscope while the endoscope is inside a hollow organ. Anyone skilled in the art would readily appreciate that a rear view catheter can also alternatively be irreversibly engaged with the endoscope while the endoscope is inside a hollow organ, while achieving the same objective of providing a rear view while the parent endoscope provides a forward view of the hollow organ. According to one embodiment, a rear view catheter is disposed inside a strategically placed rear view channel inside the shaft of the parent endoscope with a rear view channel outlet at the distal end of the parent endoscope. The rear view catheter comprises of two positions—a resting position inside the rear view hollow channel of the shaft, as illustrated in FIG. 15A, and an active position, as illustrated in FIGS. 15B and 15C, where it extends distal to the distal end of the parent endoscope—and positions the rear view image lens and/or rear view light in a rearward direction relative to the first image lens of the parent endoscope to provide a rear view of the hollow organ.

In one embodiment, as discussed above, a parent endoscope and a rear view catheter are connected to a single processor box comprising of an image processor, power source and light source (optional). Referring to FIG. 15A, in one embodiment of a disclosed rear view catheter, the proximal end of the rear view catheter has one or more female connectors. The female housing comprises one or more circular electrical connector pins. The parent endoscope has a rear view channel having a distal end and a proximal end, with the proximal end having one or more male connectors to mate or otherwise engage the corresponding female connectors of the rear view catheter (e.g., an L-catheter). Each of the male connectors comprises one or more of circular electrical connector pins that are operatively connected to one or more of image processor, power source and light source.

Referring to FIGS. 15B and 15C, when a rear view catheter is inserted into the rear view channel of the parent endoscope, the female connectors of the rear view catheter and the male connectors of the rear view channel engage, wherein the circular electrical pins of the female connectors mate with corresponding circular electrical connector pins of the male connectors. Once engaged, the connection serves as a communication link between one or more of the image processor, power source and light source and the rear view catheter. When engaged with the female connectors, the male connectors, as a whole, provides power to the image lens (CCD/CMOS) and LED lights, transmits light from the light source when a light guide is used, and transfers images from the image lens to the image processor.

As a skilled artisan readily appreciates, the configurations illustrated in FIGS. 15A-C are just exemplary. For example, the connectors of the rear view catheter may instead be male connectors, and the connectors of the rear view channel of the parent endoscope may instead be corresponding female connectors without departing from the scope and spirit of the present disclosure. Alternatively; the rear view catheter may be connected to an independent image processor and/or light source.

Reusable or Disposable Rear View Catheter or Front Rear View Module

According to one aspect of the present disclosure, reusable rear view catheter or front rear view module is at least partially permanently disposed inside the rear view hollow channel. At rest, it is disposed inside the rear view hollow channel. It is deployed in an active position by extending it beyond the distal end of the endoscope till it achieves a retroflexed/rearward position.

Figure 14A:
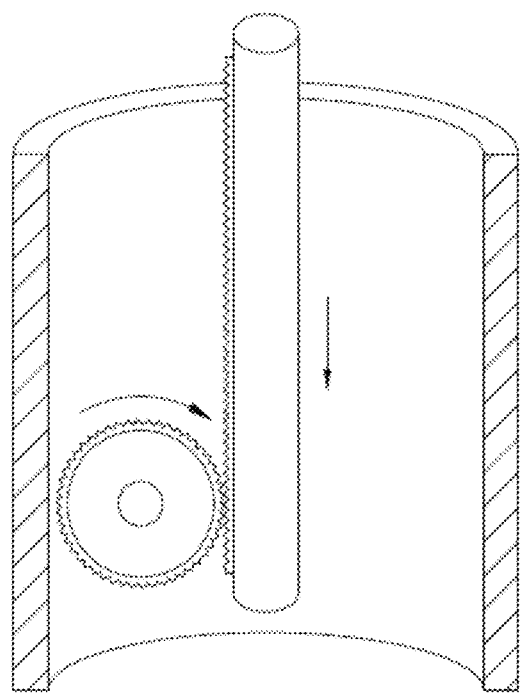
FIGS. 14A-B are perspective views with respect to the inside of an outer channel (such as an instrument channel or a dedicated channel for a rear view catheter) within a main shaft of an endoscope, illustrating an exemplary novel configuration for conveniently extending or retracting a catheter within the outer channel of the endoscope, according to one or more embodiments of the present disclosure.
Figure 14B:
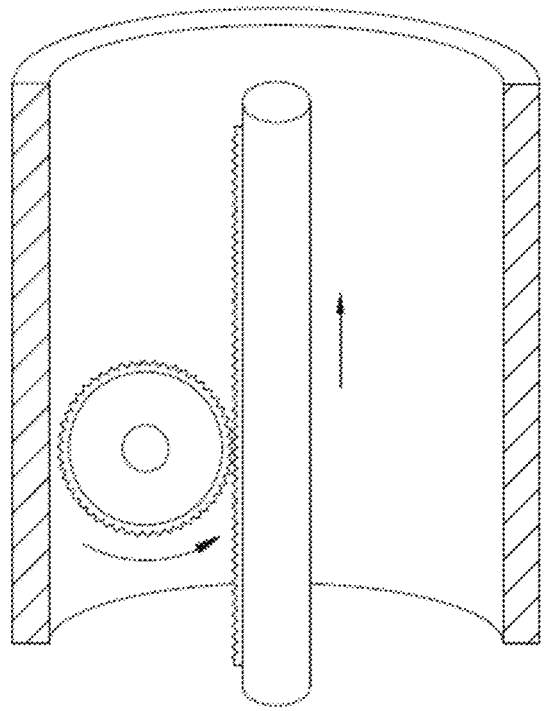

FIGS. 14A and 14B illustrate an exemplary novel configuration for conveniently extending or retracting a catheter within the outer channel of the endoscope, according to one or more embodiments of the present disclosure. Referring to FIGS. 14A and 14B, the under surface of a rear view catheter is operatively engaged to a corrugated motorized actuating wheel also disposed inside the hollow rear channel. Rotation of the actuating wheel extends and retracts a rear view catheter from the hollow rear channel, as illustrated in FIGS. 14A and 14B, respectively. This deployment method/means is only for illustration purposes, as those skilled in the art would readily recognize that other deployment method/means can be used to deploy a rear view catheter or a front rear view module without departing from the scope and spirit of the present disclosure.

Hence, the deployment method/means should not be considered limiting. While having a reusable rear view catheter may be cost effective, it may present issues with endoscope cleaning, leakage and more importantly may pose infection control issues when the same endoscope and rear view catheter/module is used on multiple patients.

A disposable rear view catheter or front rear view module is inserted into the rear view channel prior to a procedure. When a rear view catheter is desired to be deployed in retroflexed/rearview position (which is disclosed an exemplified in FIGS. 17-19 of the incorporated Applicant's U.S. Pat. No. 8,585,584), it is extended beyond distal end 100 of the endoscope. Referring to FIGS. 14A and 14B, according to one means of deployment, the under surface of the rear view catheter/front rear view module is operatively engaged to a corrugated motorized actuating wheel also disposed inside the hollow rear channel. Rotation of the actuating wheel extends and retracts a rear view catheter from the hollow rear channel. This deployment method/means is only for illustration purposes. As those skilled in the art would readily recognize that other deployment method/means can be easily used to deploy the rear view catheter/front rear view module. Hence the deployment method/means should not be considered limiting.

Once the procedure is completed, the rear view catheter or front rear view module is disengaged from the rear view hollow channel and disposed. In one embodiment, the rear view catheter/front rear view module is disengaged by manually pulling it out (with or without rotational movement of the rear view catheter or front rear view module)

from within the rear view hollow channel from the distal end of the shaft. As illustrated in FIGS. 15A-C, a stop measure (e.g., in the form of one or more stop plugs, as illustrated in FIGS. 15A-C), is provided at the distal end of the rear view hollow channel to prevent the rear view catheter or front rear view module from completely migrating out of the rear view hollow channel when it is extended beyond the distal end of the endoscope to acquire retroflexed/rearview position. Once the rear view catheter/front rear view module is disengaged from the endoscope, the rear view channel can be easily cleaned and/or sterilized using standard endoscope channel cleaning methods.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims.

What is claimed is:

1. An endoscope system comprising:
an endoscope having a single shaft having a distal end receivable in a hollow gastrointestinal tract and a proximal end, the shaft extending from the proximal end along a longitudinal axis in a forward direction towards the distal end, the distal end having an end surface defining a vertical reference plane orthogonal to the longitudinal axis, the endoscope having, at or near the distal end, multiple cameras disposed when in operation, each of the multiple cameras having a different respective field of view (FOV), the multiple cameras including a subset of at least two side view cameras each disposed on a respective side periphery of the single shaft and having a respective sideward FOV including a respective obtuse angle to the forward direction of the longitudinal axis, the multiple cameras further including one front view camera disposed facing the forward direction of the longitudinal axis and having a frontward FOV, the multiple cameras further including a rear view camera disposed in front of the distal end, facing a rearward direction of the longitudinal axis, and having a rearward FOV covering at least one portion of the end surface of the distal end; and
an image processing box adapted to receive respective images of the different respective FOVs from the respective multiple cameras and process the received respective image to form a consolidated image using image-stitching techniques, the consolidated image configured to cover a 360-degree view with respect to at least one point on the end surface of the distal end, the 360-degree view being in a horizontal reference plane orthogonal to the vertical reference plane, the horizontal reference plane being in parallel to, or encompassing, the longitudinal axis.

2. The endoscope system as claimed in claim 1, wherein the rear view camera is disposed in front of the distal end through a deployment performed using a catheter extended inside through the hollow channel.

3. The endoscope system as claimed in claim 1, wherein the consolidated image includes a first component image situated separate and next to a second component image formed using the respective images of the different respective FOVs received from the front view camera and the subset of at least two side view cameras, the second component image being a consolidated component image formed using image-stitching techniques, the first component image formed using the respective image of the respective FOV received from the rear view camera, the subset of at least two side view cameras including at least four side view cameras each having one respective representative point intersecting with a respective vertical cross section plane situated in parallel to the vertical reference plane of the end surface of the distal end, each of the four respective representative points, in reference to the vertical reference plane through projection, being ninety (90) degrees relative to one adjacent representative point of the four respective representative points with respect to a center point on the vertical reference plane.

4. The endoscope system as claimed in claim 3, the second component image, which is a consolidated component image, is configured to have, in a center area thereof, a center sub-component image formed using the respective image of the frontward FOV of the front view camera, and is further configured to have four sub-component images respectively formed using the images of the four sideward FOVs of the subset of four side view cameras and collectively surround the center sub-component image.

* * * * *